(12) United States Patent
Velis et al.

(10) Patent No.: US 11,890,225 B2
(45) Date of Patent: *Feb. 6, 2024

(54) DEVICES AND METHODS FOR SLURRY GENERATION

(71) Applicant: Miraki Innovation Think Tank LLC, Cambridge, MA (US)

(72) Inventors: Christopher Velis, Lexington, MA (US); Cole C. Velis, Cambridge, MA (US); Karen Miller, South Dartmouth, MA (US)

(73) Assignee: MIRAKI INNOVATION THINK TANK LLC, Cambridge, MA (US)

( * ) Notice: Subject to any disclaimer, the term of this patent is extended or adjusted under 35 U.S.C. 154(b) by 281 days.

This patent is subject to a terminal disclaimer.

(21) Appl. No.: 17/219,240

(22) Filed: Mar. 31, 2021

(65) Prior Publication Data

US 2021/0275351 A1 Sep. 9, 2021

Related U.S. Application Data

(63) Continuation of application No. 15/798,489, filed on Oct. 31, 2017, now Pat. No. 11,000,409.

(Continued)

(51) Int. Cl.
*A61F 7/12* (2006.01)
*A61F 7/00* (2006.01)

(52) U.S. Cl.
CPC ............. *A61F 7/12* (2013.01); *A61F 7/0085* (2013.01); *A61F 2007/0063* (2013.01); *A61F 2007/126* (2013.01)

(58) Field of Classification Search
CPC ...................................................... A61M 5/44
See application file for complete search history.

(56) References Cited

U.S. PATENT DOCUMENTS 3,373,906 A   3/1968   Hart et al.
3,893,834 A   7/1975   Armstrong
(Continued)

FOREIGN PATENT DOCUMENTS

CN   102307545   1/2012
CN   103110473   5/2013
(Continued)

OTHER PUBLICATIONS

Office Action dated Jun. 29, 2021 in Japanese Application No. 2019-544798 With English translation thereof.
Ash, 2003, Chronic peritoneal dialysis catheters: overview of design, placement, and removal procedures, Int Nephrol Dialysis 16(4):323-34.

(Continued)

*Primary Examiner* — Kaitlyn E Smith
(74) *Attorney, Agent, or Firm* — Wenderoth, Lind & Ponack, L.L.P.

(57) ABSTRACT

The present invention involves the use of a small profile device for preparation and/or delivery of cold slurry into the human body. The cold slurry can be generated within the device itself or within a separate small chamber, both of which produce a cold slurry using a cooling source and an injectable fluid. The delivery device provides continued agitation to the fluid/slurry through rotation and/or vibration of blades within the device. The fluid/cold slurry is cooled/kept cool through the use of an external cooling device, such as a cooling sleeve, that at least partially surrounds the delivery device. The cooling sleeve can cool or maintain the temperature of the cold slurry through a number of mechanisms. The cold slurry can be delivered using a device in accordance with the present invention to any tissue inside the body, including subcutaneous fat, visceral fat, and brown fat.

31 Claims, 14 Drawing Sheets

Related U.S. Application Data

(60) Provisional application No. 62/416,484, filed on Nov. 2, 2016.

(56) References Cited

U.S. PATENT DOCUMENTS

| | | |
|---|---|---|
| 4,619,678 A | 10/1986 | Rubin |
| 4,983,045 A | 1/1991 | Taniguchi |
| 4,986,079 A | 1/1991 | Koseki et al. |
| 5,143,063 A | 9/1992 | Fellner |
| 5,304,128 A | 4/1994 | Haber et al. |
| 5,507,790 A | 4/1996 | Weiss |
| 5,769,879 A | 6/1998 | Richards et al. |
| 6,032,675 A | 3/2000 | Rubinsky |
| 6,041,787 A | 3/2000 | Rubinsky |
| 6,067,803 A | 5/2000 | Wolsey |
| 6,244,052 B1 | 6/2001 | Kasza |
| 6,300,130 B1 | 10/2001 | Toner et al. |
| 6,324,863 B1 | 12/2001 | Henry |
| 6,334,328 B1 | 1/2002 | Brill |
| 6,403,376 B1 | 6/2002 | Toner et al. |
| 6,413,444 B1 | 7/2002 | Kasza |
| 6,430,957 B1 | 8/2002 | Inada et al. |
| 6,475,212 B2 | 11/2002 | Dobak, III et al. |
| 6,547,811 B1 | 4/2003 | Becker et al. |
| 6,673,607 B2 | 1/2004 | Toner et al. |
| 6,849,072 B2 | 2/2005 | Lee et al. |
| 6,962,601 B2 | 11/2005 | Becker et al. |
| 7,118,591 B2 | 10/2006 | Frank et al. |
| 7,367,341 B2 | 5/2008 | Anderson et al. |
| 7,389,653 B2 | 6/2008 | Kasza et al. |
| 7,422,601 B2 | 9/2008 | Becker et al. |
| 7,507,234 B2 | 3/2009 | Utley et al. |
| 7,588,547 B2 | 9/2009 | Deem et al. |
| 7,603,868 B2 | 10/2009 | Sveinsson |
| 7,681,411 B2 | 3/2010 | DiLorenzo |
| 7,713,266 B2 | 5/2010 | Elkins et al. |
| 7,854,754 B2 | 12/2010 | Ting et al. |
| 8,117,854 B2 | 2/2012 | Lampe et al. |
| 8,192,474 B2 | 6/2012 | Levinson |
| 8,275,442 B2 | 9/2012 | Allison |
| 8,285,390 B2 | 10/2012 | Levinson et al. |
| 8,298,216 B2 | 10/2012 | Burger et al. |
| 8,308,681 B2 | 11/2012 | Slocum |
| 8,337,539 B2 | 12/2012 | Ting et al. |
| 8,505,315 B2 | 8/2013 | Kasza et al. |
| 8,523,927 B2 | 9/2013 | Levinson et al. |
| 8,603,073 B2 | 12/2013 | Allison |
| 8,608,696 B1 | 12/2013 | DiMeo et al. |
| 8,676,338 B2 | 3/2014 | Levinson |
| 8,702,774 B2 | 4/2014 | Baker et al. |
| 8,808,241 B2 | 8/2014 | DiMeo et al. |
| 8,840,608 B2 | 9/2014 | Anderson et al. |
| 8,974,451 B2 | 3/2015 | Smith |
| 9,044,212 B2 | 6/2015 | LePivert |
| 9,078,634 B2 | 7/2015 | Gonzales et al. |
| 9,132,031 B2 | 9/2015 | Levinson et al. |
| 9,314,368 B2 | 4/2016 | Allison et al. |
| 9,345,526 B2 | 5/2016 | Elkins et al. |
| 9,375,345 B2 | 6/2016 | Levinson et al. |
| 9,398,930 B2 | 7/2016 | Leung et al. |
| 9,408,745 B2 | 8/2016 | Levinson et al. |
| 9,522,031 B2 | 12/2016 | Anderson et al. |
| 9,545,523 B2 | 1/2017 | Nanda |
| 9,585,687 B2 | 3/2017 | Tenenbaum et al. |
| 9,649,220 B2 | 5/2017 | Anderson et al. |
| 9,655,770 B2 | 5/2017 | Levinson et al. |
| 9,656,056 B2 | 5/2017 | Boyden et al. |
| 10,174,985 B2 | 1/2019 | Arnitz |
| 10,406,021 B2 | 9/2019 | Wu |
| 10,500,342 B2 | 12/2019 | Velis |
| 11,000,409 B2 * | 5/2021 | Velis .................. A61M 5/44 |
| 2002/0107199 A1 | 8/2002 | Walker |
| 2003/0012079 A1 | 1/2003 | Coffeen et al. |
| 2003/0032996 A1 | 2/2003 | Hallman |
| 2003/0074903 A1 | 4/2003 | Upadhye et al. |
| 2003/0171715 A1 | 9/2003 | Hommann |
| 2004/0199115 A1 | 10/2004 | Rosenman |
| 2005/0203598 A1 | 9/2005 | Becker et al. |
| 2005/0251120 A1 | 11/2005 | Anderson et al. |
| 2006/0036302 A1 | 2/2006 | Kasza et al. |
| 2006/0161232 A1 | 7/2006 | Kasza et al. |
| 2007/0010861 A1 | 1/2007 | Anderson et al. |
| 2007/0056313 A1 | 3/2007 | Kasza et al. |
| 2007/0106247 A1 | 5/2007 | Burnett et al. |
| 2007/0198071 A1 | 8/2007 | Ting et al. |
| 2007/0255362 A1 | 11/2007 | Levinson et al. |
| 2007/0270925 A1 | 11/2007 | Levinson |
| 2008/0077201 A1 | 3/2008 | Levinson et al. |
| 2008/0077202 A1 | 3/2008 | Levinson |
| 2008/0077211 A1 | 3/2008 | Levinson et al. |
| 2008/0161757 A1 | 7/2008 | Nayak et al. |
| 2008/0236186 A1 | 10/2008 | Kasza et al. |
| 2008/0287839 A1 | 11/2008 | Rosen et al. |
| 2009/0018623 A1 | 1/2009 | Levinson et al. |
| 2009/0018624 A1 | 1/2009 | Levinson et al. |
| 2009/0018625 A1 | 1/2009 | Levinson et al. |
| 2009/0018626 A1 | 1/2009 | Levinson et al. |
| 2009/0018627 A1 | 1/2009 | Levinson et al. |
| 2009/0118722 A1 | 5/2009 | Ebbers et al. |
| 2009/0125087 A1 | 5/2009 | Becker et al. |
| 2009/0149929 A1 | 6/2009 | Levinson et al. |
| 2009/0255276 A1 | 10/2009 | Kasza et al. |
| 2010/0036295 A1 | 2/2010 | Altshuler et al. |
| 2010/0081971 A1 | 4/2010 | Allison |
| 2010/0152824 A1 | 6/2010 | Allison |
| 2010/0152880 A1 | 6/2010 | Boyden et al. |
| 2010/0280582 A1 | 11/2010 | Baker et al. |
| 2010/0308257 A1 | 12/2010 | Lampe et al. |
| 2011/0066216 A1 | 3/2011 | Ting et al. |
| 2011/0238050 A1 | 9/2011 | Allison et al. |
| 2011/0238051 A1 | 9/2011 | Levinson et al. |
| 2011/0300079 A1 | 12/2011 | Martens et al. |
| 2012/0000217 A1 | 1/2012 | Gudnason |
| 2012/0022518 A1 | 1/2012 | Levinson |
| 2012/0092951 A1 | 4/2012 | Faccioli et al. |
| 2012/0239123 A1 | 9/2012 | Weber et al. |
| 2013/0066309 A1 | 3/2013 | Levinson |
| 2013/0079684 A1 | 3/2013 | Rosen et al. |
| 2013/0116758 A1 | 5/2013 | Levinson et al. |
| 2013/0116759 A1 | 5/2013 | Levinson et al. |
| 2013/0158440 A1 | 6/2013 | Allison |
| 2013/0158636 A1 | 6/2013 | Ting et al. |
| 2013/0190744 A1 | 7/2013 | Avram et al. |
| 2013/0231609 A1 | 9/2013 | Slocum et al. |
| 2013/0245731 A1 | 9/2013 | Allison |
| 2013/0253496 A1 | 9/2013 | Anderson et al. |
| 2014/0005760 A1 | 1/2014 | Levinson et al. |
| 2014/0030697 A1 | 1/2014 | Ploegh et al. |
| 2014/0067025 A1 | 3/2014 | Levinson et al. |
| 2014/0091113 A1 | 4/2014 | Brewster et al. |
| 2014/0200511 A1 | 7/2014 | Boyden et al. |
| 2014/0257443 A1 | 9/2014 | Baker et al. |
| 2014/0277219 A1 | 9/2014 | Baker et al. |
| 2014/0277302 A1 | 9/2014 | Weber et al. |
| 2014/0303696 A1 | 10/2014 | Anderson et al. |
| 2014/0316393 A1 | 10/2014 | Levinson |
| 2014/0358079 A1 | 12/2014 | Fischell et al. |
| 2015/0112195 A1 | 4/2015 | Berger et al. |
| 2015/0216816 A1 | 8/2015 | O'Neil et al. |
| 2015/0297246 A1 | 10/2015 | Patel et al. |
| 2015/0320938 A1 | 11/2015 | King et al. |
| 2015/0328077 A1 | 11/2015 | Levinson |
| 2015/0342780 A1 | 12/2015 | Levinson et al. |
| 2015/0343156 A1 | 12/2015 | Fischell et al. |
| 2016/0051401 A1 | 2/2016 | Yee et al. |
| 2016/0058956 A1 | 3/2016 | Cohn et al. |
| 2016/0089550 A1 | 3/2016 | DeBenedictis et al. |
| 2016/0112195 A1 | 4/2016 | Jochheim et al. |
| 2016/0128767 A1 | 5/2016 | Azamian et al. |
| 2016/0175141 A1 | 6/2016 | Wu et al. |
| 2016/0242661 A1 | 8/2016 | Fischell et al. |
| 2016/0317621 A1 | 11/2016 | Bright |
| 2016/0354137 A1 | 12/2016 | Fischell et al. |
| 2016/0354237 A1 | 12/2016 | Gonzales et al. |

(56) References Cited

U.S. PATENT DOCUMENTS

| | | |
|---|---|---|
| 2017/0035603 A1 | 2/2017 | Kammer |
| 2017/0105869 A1 | 4/2017 | Frangineas, Jr. |
| 2017/0136237 A1 | 5/2017 | Eckhouse et al. |
| 2017/0143538 A1 | 5/2017 | Lee et al. |
| 2017/0164965 A1 | 6/2017 | Chang et al. |
| 2017/0202613 A1 | 7/2017 | Pellegrino et al. |
| 2017/0246032 A1 | 8/2017 | Gonzales et al. |
| 2017/0274011 A1 | 9/2017 | Garibyan et al. |
| 2017/0325992 A1 | 11/2017 | DeBenedictis et al. |
| 2018/0140514 A1 | 5/2018 | Velis |
| 2019/0053939 A1* | 2/2019 | Garibyan .............. A61M 5/158 |
| 2019/0054242 A1 | 2/2019 | Velis |
| 2020/0086054 A1 | 3/2020 | Velis |
| 2020/0113627 A1 | 4/2020 | Alas |
| 2020/0114041 A1 | 4/2020 | Alas |

FOREIGN PATENT DOCUMENTS

| | | |
|---|---|---|
| CN | 204050541 | 12/2014 |
| CN | 105640706 | 6/2016 |
| EP | 0418979 | 3/1991 |
| EP | 0 445 951 | 9/1991 |
| ES | 2 421 545 | 9/2013 |
| GB | 2 338 428 | 12/1999 |
| GB | 2529867 | 3/2016 |
| JP | 2008-529663 | 8/2008 |
| KR | 10-2015-0127179 | 11/2015 |
| WO | 2006/086479 | 8/2006 |
| WO | 2008/017456 | 2/2008 |
| WO | 2009/089090 | 7/2009 |
| WO | 2013/113970 | 8/2013 |
| WO | 2014/165058 | 10/2014 |
| WO | 2016/033380 | 3/2016 |
| WO | 2016/033384 | 3/2016 |
| WO | 2016/054165 | 4/2016 |
| WO | 2016/090175 | 6/2016 |
| WO | 2017/196548 | 11/2017 |

OTHER PUBLICATIONS

Brink, 2008, Abdominoplasty with direct resection of deep fat, Plast Reconstructive Surg 123(5):1597-1603.
Ding, 2008, The association between non-subcutaneous adiposity and calcified coronary plaque: A substudy of the multi-ethnic study of atherosclerosis, Am J Clin Nutr 88(3):645-650.
Fox, 2007, Abdominal visceral and subcutaneous adipose tissue compartments-associationwith metabolic risk actors in the Framingham heart study, Circulation 116:39-48.
Garaulet, 2006, Relationship between fat cell size and number and fatty acid composition in adipose tissue from different fat depots in overweighUobese humans, Int J Obes 30(6):899-905.
Gradinger, 2005, Abdominoplasty, Chapter 83, pp. 2935-3026, in The art of aesthetic surgery: principles & techniques, Nahai, Ed., Quality Med Pub, St. Louis Mo. (92 pages).
International Preliminary Report on Patentability dated Aug. 21, 2012, for International application No. PCT/US2011/24766, filed Feb. 14, 2011 (8 pages).
International Search Report and Written Opinion dated Apr. 12, 2011, for International Application No. PCT/US11/24766, filed Feb. 14, 2011 (11 pages).
Laven, 2006, A pilot study of ice-slurry application for inducing laparoscopic renal hypothermia, BJU In!99:166-70.
Laverson, 2006, Improving abdominoplasty results: reconstruction of the linea alba sulcus by direct excision, Aesthetic Surg J 26:682-6.
Stevens, 2014, "Does cryolipolysis lead to skin tightening?A first report of cryodermadstringo", Aesth Surg J 34(6):NP32-NP34.
Yamamoto, 2010, Adipose depots possess unique developmental gene signatures, Obesity 18{5}:872-78.
Written Opinion dated Jul. 1, 2020 in Singapore Application No. 11201903946S.
Extended European Search Report dated Aug. 28, 2020 in European Application No. 17868153.2.
Office Action dated Mar. 1, 2021 in Chinese Application No. 2017800786800 (with English translation).

* cited by examiner

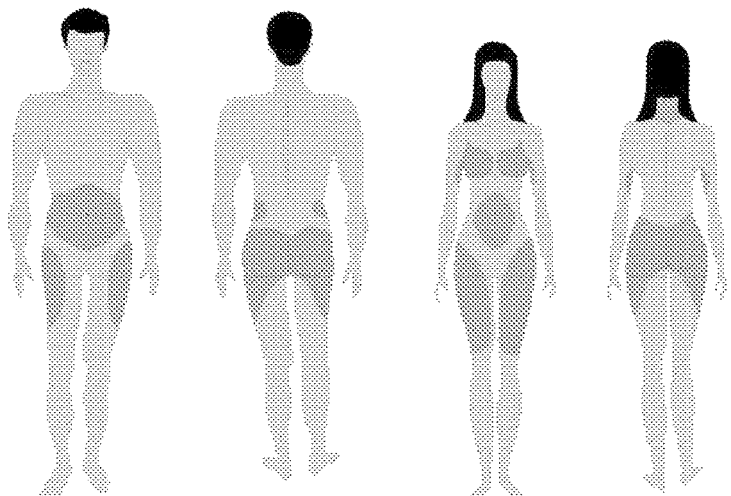
FIG. 1A
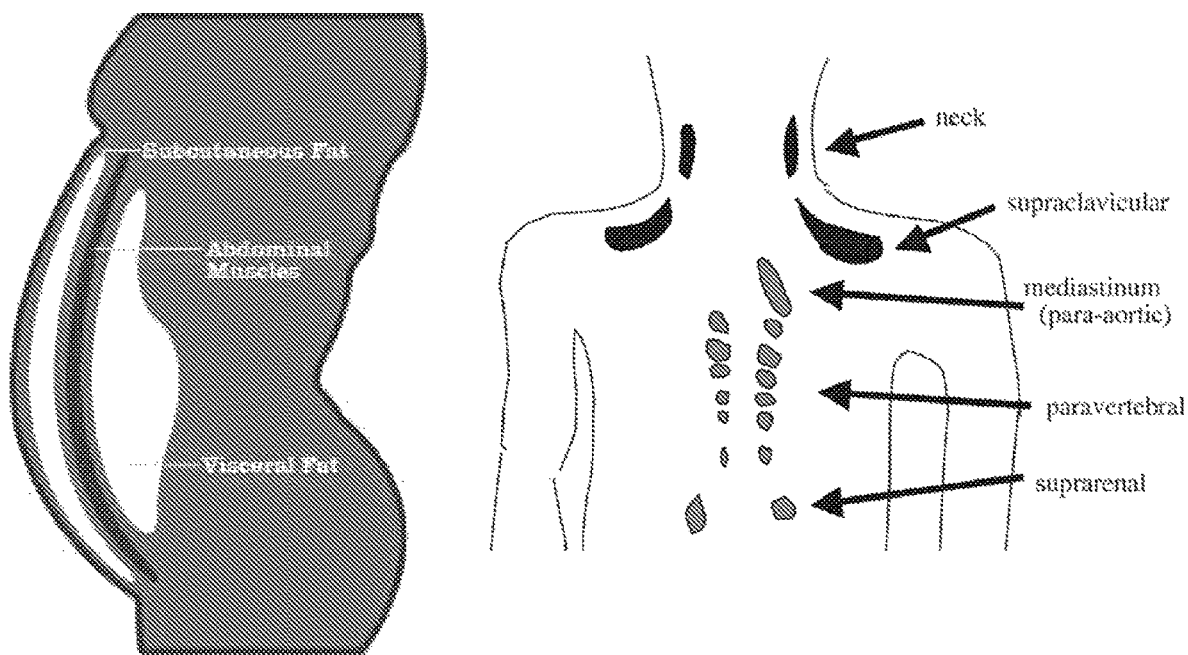
FIG. 1B
FIG. 1C

DEVICES AND METHODS FOR SLURRY GENERATION

BACKGROUND

The demand for procedures to reduce fat, often referred to as body contouring procedures, is large and continues to rise, especially with the increasing number of minimally and non-invasive therapies available. According to the American Society of Aesthetic Plastic Surgery (ASAPS), in 2014, consumers spent approximately $12 billion on aesthetic procedures, including invasive, minimally-invasive, and non-invasive fat reduction procedures.

Invasive fat reduction procedures on the market include liposuction, abdominoplasty ("tummy tuck"), gluteoplasty (buttock lifts), brachioplasty (arm lift), thighplasty (thigh lift), lower rhytidectomy (neck lift), and mentoplasty (chin tightening). Invasive therapies carry risks associated with surgical procedures, some of which can be life threatening. These include infection, scarring, perforation of organs and vessels, and hemorrhage. Additionally, invasive therapies are often painful and typically require a lengthy recovery period.

Minimally-invasive fat reduction procedures include laser-assisted liposuction, laser lipolysis (i.e., the breakdown of lipids), radio frequency lipolysis, ultrasound lipolysis, and injection lipolysis (e.g. injection of deoxycholic acid; KYBELLA). These procedures may require a surgical incision and/or the delivery of chemicals into the body, which can carry risks to the patient, and are often painful and produce non-uniform results.

Noninvasive procedures currently on the market include the use of radio frequency, lasers, and ultrasound as well as the application of cold temperatures to the surface of the skin (e.g. COOLSCULPTING by Zeltiq Aesthetics, Inc.). These therapies are often time consuming and painful, while delivering minimal results.

Recently, minimally and non-invasive procedures to delivery cold to fat tissue have been developed, with a non-invasive therapy known as CoolSculpting, as noted above, currently on the market. These procedures are based on the principle that fat cells (adipose tissue) are more sensitive to cold temperatures than the skin or other surrounding tissues, with the cold temperatures causing the fat cells to undergo apoptosis, a natural biological process through which fat cells are eliminated from the body.

Non-invasive delivery of cool temperatures to the skin can be painful, may produce unsatisfactory results, and is very time consuming, with the associated apparatus needing to be held on a patient's skin for a lengthy amount of time. In contrast, delivery of a cold liquid such as a slurry, to the fat cells subdermally (or deeper to visceral fat tissues) provide a safe, controlled means for effective and selective reduction of fat cells. Methods for preparing a cold slurry and for delivering a cold liquid to fat tissue through a cannula are disclosed in International Application Publication No. WO/2016/033380 and U.S. Patent Application Publication No. 2013/0190744, each of which is incorporated herein in its entirety. However, there exists a need for a cold slurry point of care delivery device that is convenient, requires minimal maintenance and square footage, and is the least minimally invasive to the patient.

SUMMARY

The present invention provides for a convenient means for generating a cold slurry using an apparatus that has minimal parts and does not require extensive setup, expensive maintenance, or refrigerated transportation/on-site storage. The apparatus and methods of the present invention also provide targeted delivery of a cold slurry to fat cells without requiring a surgical incision.

Generally, the present invention involves the use of a small profile apparatus for preparation and/or delivery of cold slurry to the human body. The cold slurry can be generated within the device itself or within a separate small chamber, both of which produce a cold slurry at the point of care using a cooling source and an injectable fluid. When the cold slurry is produced in a separate chamber, it can then be easily transferred to the delivery device, which can be a syringe-type device. The delivery device is capable of providing continued agitation to the fluid/slurry at the point of care, such as through rotation of blades within the device, use of vibration or both. The fluid/cold slurry is cooled/kept cool inside the delivery device through the use of a small profile external cooling device, such as a cooling sleeve, that at least partially surrounds the device to provide cooling at the point of care. The cooling sleeve can cool or maintain the temperature of the cold slurry through a number of mechanisms, such as the provision of a refrigerant, the triggering of an endothermic reaction, and the compression of gas. The cold slurry can be delivered using an apparatus in accordance with the present invention to any fat tissue inside the body, including subcutaneous, visceral, and brown fat. See, for example, FIGS. 1A and 1B for diagrams of subcutaneous fat locations, as well as subcutaneous and visceral fat locations within the abdominal area. For example, the cold slurry can be delivered to, for example but not limited to, fat tissue around the flank (i.e. "love handles"), abdomen, thigh area, upper arm, submental area under the chin, sub orbital fat pockets, above the knees, and any other pockets of subcutaneous fat for which reduction of the fat would be desirable.

In certain embodiments, the invention provides an apparatus for the production and/or delivery of a cold slurry. The apparatus includes a cylindrical member comprising a first end, a second end, and a longitudinal axis extending through the first and second ends. The apparatus further includes an outer surface extending between the first and second ends along the longitudinal axis, and an interior lumen defined by an interior wall of the cylindrical member. The interior lumen is configured to receive and hold a cold slurry. The apparatus further includes a plunger that is at least partially disposed within the interior lumen and configured to move within the cylindrical member in the direction of the longitudinal axis. The plunger includes a head, a plunging member, and a rod extending between the head and the plunging member along the longitudinal axis of the cylindrical member. The apparatus further includes at least one needle extending from the second end of the cylindrical member and an agitation device coupled to the plunger. The agitation device is configured to agitate the cold slurry within the interior lumen of the cylindrical member.

The apparatus can further include a motor coupled to the plunger. The motor can coupled to the rod between the head and the plunging member. The motor can be coupled to the head of the plunger.

The agitation device can include at least one rotation blade extending from the plunging member towards the second end of the cylindrical member. The agitation device is configured to agitate the cold slurry upon rotation of the plunger. The agitation device can include a wire extending from the plunging member towards the second end of the cylindrical member along the longitudinal axis. The agitation device can further include one or more tentacles extending out from the wire and toward the interior wall of the cylindrical member. The agitation device can further include a motor coupled to the plunger and configured to vibrate the wire.

The outer surface of the cylindrical member can include a conductive material, such as copper.

The apparatus can further include a sheath surrounding the cylindrical member. The sheath can include a conductive material, such as copper.

The apparatus can further include a cooling sleeve surrounding at least a portion of the cylindrical member. The cooling sleeve is configured to cool or maintain a temperature of the cold slurry within the interior lumen of the cylindrical member. The cooling sleeve and the cylindrical member can be in a concentric arrangement with a space formed between an inner surface of the cooling sleeve and the outer surface of the cylindrical member.

The apparatus can further include at least one tubular member located within the space. The tubular member is disposed axially about and extending at least partially around a circumference of the outer surface of the cylindrical member. The tubular member is configured to contain a cooling fluid. The tubular member can be in the shape of a coil.

The apparatus can further include a container surrounding at least a portion of the cooling sleeve and fluidically connected to the tubular member at least one location. The container is configured to hold a cooling fluid and supply the cooling fluid to the tubular member.

The cooling sleeve can further include a cap configured to engage with and rotate the plunger of the cylindrical member.

The apparatus can further include a cap around the first end of the cylindrical member. The cap is configured to seat with the cooling sleeve towards the first end of the cylindrical member. A seal is provided between the cap and the cooling sleeve. A first chemical can be provided within an interior space of the cap and a second chemical can be provided within the space between the cylindrical member and the cooling sleeve. In this embodiment, the seal separates the first chemical from the second chemical. An endothermic reaction occurs when the first chemical and the second chemical are mixed together. The first chemical and second chemical can be selected from the group consisting of: water, ammonium chloride, potassium nitrate, sodium thiosulphate, ammonium nitrate, ammonium thiocyanate, and barium hydroxide octahydrate.

In some embodiments, the space between the cylindrical member and the cooling sleeve can forms a chamber. A container surrounding at least a portion of the cooling sleeve is fluidically connected to the chamber. The container is configured to hold a cooling fluid and supply the cooling fluid to the chamber. At least one inlet located between the chamber and the container is configured to allow the cooling fluid to flow from the container and into the chamber. The at least one inlet can be operably coupled to a release mechanism to control the flow of the cooling fluid through the inlet.

The apparatus can further include a conductive membrane provided between the chamber and the outer surface of the cylindrical member. The outer surface of the cylindrical member can include a conductive material. The conductive membrane and the conductive material can be configured to interact with each other when the cylindrical member is received within the cooling sleeve.

In certain embodiments, the apparatus includes at least one chamber disposed within the space between the inner surface of the cooling sleeve and the outer surface of the cylindrical member. The at least one chamber extends along a second axis parallel to the longitudinal axis of the cylindrical member and is configured to contain a fluid. The apparatus further includes a pressurized gas source configured to compress the fluid in the at least one chamber. The at least one chamber can include a second plunger configured to compress the fluid when activated by the pressurized gas source. At least a portion of a wall of the at least one chamber that faces the cylindrical member can include a conductive membrane.

The apparatus can include a chamber configured to removably couple and supply the cold slurry to the interior lumen of the cylindrical member. The chamber can include a top end and a bottom end. The top end includes a first connector that mates with a second connector located at the second end of the cylindrical member. The first connector and the second connector are configured to allow the cold slurry to flow from the chamber and into the interior lumen when mated.

The chamber can be configured to produce the cold slurry using a cooling fluid that cools an injectable fluid. The chamber can include a first compartment located at the top end of the chamber and configured to contain the injectable fluid, a second compartment located between the top and bottom ends of the chamber, and a third compartment located at the bottom end of the chamber and configured to contain the cooling fluid. The second compartment can be configured to contain salt water filled particles. The first compartment and the second compartment can be separated from each other by a separation member. The separation member can be a breakable seal configured to break, such that a content of the second chamber mixes with the injectable fluid in the first compartment.

In some embodiments, the second compartment and the third compartment are in fluidic communication with each other through one or more valves. The one or more valves are configured to release the cooling fluid in the third compartment into the second compartment when the one or more valves are opened.

In other embodiments, the invention provides an apparatus for the production of a cold slurry for delivery to a tissue within a patient's body. The apparatus includes a first compartment containing an injectable fluid, a second compartment, and a third compartment containing a cooling fluid, which is provided to cool the injectable fluid. The second compartment can include a plurality of particles, which in some embodiments; can be a plurality of salt water filled particles. The first compartment and the second compartment can be separated from each other by a separation member. The separation member can be a breakable seal configured to break, such that a content of the second chamber mixes with the injectable fluid in the first compartment. The second compartment and the third compartment can be in fluidic communication with each other through one or more release mechanisms. The release mechanisms are configured to release the cooling fluid in the third compartment into the second compartment when the release mechanisms are triggered.

In certain embodiments, the present invention provides a method of generating a cold slurry using a delivery device. The method includes providing a fluid to an interior lumen of a cylindrical member of a delivery device, agitating the fluid within the interior lumen using an agitation device, and cooling the fluid within the interior lumen to generate cold slurry using an external cooling device. The external cooling device at least partially surrounds the cylindrical member of the delivery device. The agitating and cooling of the fluid can be done, concurrently. The external cooling device can be a cooling sleeve surrounding at least a portion of the cylindrical member of the delivery device. The agitation device can include one or more rotation blades coupled to a plunger that is at least partially disposed within the interior lumen of the cylindrical member of the delivery device. The agitation device can include a vibration mechanism.

In some embodiments, the method further includes ejecting the cold slurry from the delivery device using a plunger that is at least partially disposed within the interior lumen of the cylindrical member of the delivery device. The ejected cold slurry can be delivered to one or more tissue types selected from the group consisting of: subcutaneous fat, visceral fat, and brown fat. The ejected cold slurry can be delivered to tissue in one or more areas selected from the group consisting of: tissue around the flank, abdomen, thigh area, upper arm, submental area under the chin, sub orbital fat pockets, above the knees, and any other pockets of subcutaneous fat for which reduction of the fat would be desirable.

In certain embodiments, the present invention provides a method of generating a cold slurry using a slurry generation chamber. The method includes providing a slurry generation chamber comprising: a first compartment containing an injectable fluid, a second compartment, and a third compartment containing a cooling fluid. The method further includes releasing the cooling fluid from the third compartment into the second compartment to cool the injectable fluid in the first compartment and generate cold slurry. The second compartment can include a plurality of particles configured to agitate the injectable fluid while the cold slurry is being generated. The method can further include releasing contents of the second compartment into the first compartment subsequent to the release of the cooling fluid from the third compartment into the second compartment. The method can further include providing agitation to the slurry generation chamber, such as shaking the slurry generation chamber.

BRIEF DESCRIPTION OF DRAWINGS

FIG. 1A is a diagram of subcutaneous fat locations in the body.

FIG. 1B is a diagram of subcutaneous and visceral fat locations within the abdominal area.

FIG. 1C is a diagram of brown fat locations in the body.

FIG. 3 shows a perspective view of a cold slurry delivery apparatus with an agitation device in accordance with an embodiment of the present invention, while

DETAILED DESCRIPTION

Figure 2:
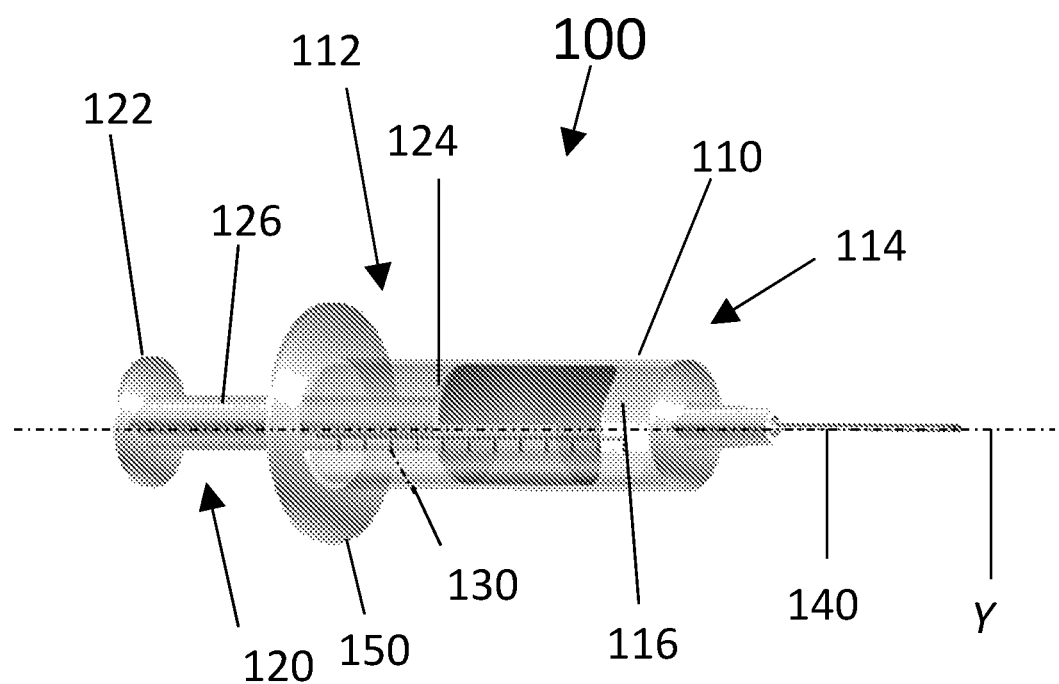
FIG. 2 shows a side view of an exemplary cold slurry delivery device.

The present invention involves the use of a small profile apparatus for preparation and delivery of cold slurry to the human body. The cold slurry can be generated in the delivery device itself or can be generated in and transferred from a separate chamber. Both methods for generating the slurry include the use of an injectable fluid, a cooling source, and some form of agitation. When a separate chamber is used, the cold slurry is produced by combining, for example a cooling source, such as a refrigerant, an injectable fluid, and an optional solid salt water source within the chamber. When the cold slurry delivery device is used to generate the cold slurry, the slurry is produced by external cooling of an injectable fluid within the device. An example of an external cooling device is a cooling sleeve that cools fluid within the device or maintains the temperature of the cold slurry delivered to the device. The cooling sleeve can cool or maintain the temperature of the cold slurry through a number of mechanisms, such as the provision of a refrigerant, the triggering of an endothermic reaction, and the compression of gas. Both the cold slurry delivery device and the separate chamber are capable of providing continued agitation to the fluid/slurry, such as through rotation of blades within the device, use of vibration, or both. The fluid/slurry is cooled/kept cool inside the cold slurry device by the use of external cooling, such as a cooling sleeve that easily slips over the device and provides cooling. The cold slurry can be delivered using an apparatus in accordance with the present invention to any fat tissue inside the body, including subcutaneous, visceral, and brown fat. For example but not limited to, the cold slurry can be delivered to fat tissue in any of the areas shown in FIGS. 1A-C, such as around the flank (i.e. "love handles"), abdomen, thigh area, upper arm, and submental area under the chin, sub orbital fat pockets, above the knees, and other areas as shown in the figures. In principle, the cold slurry can be delivered to any pockets of subcutaneous fat for which reduction of the fat would be desirable.

In one embodiment, cold slurry is generated within the cold slurry delivery device. The slurry is generated by providing a fluid to the cold slurry delivery device and cooling the fluid within the device while providing agitation. The fluid provided to the cold slurry delivery device can be any sterile, biocompatible fluid that is capable of being cooled to provide a cold slurry. Alternatively, the cold slurry can be provided to the delivery device after being produced in a separate chamber. Preferably the temperature of the fluid is cooled to or below about 10° C., 7° C., 5° C., 4° C., 3° C., 2° C., 1° C., 0° C., −1° C., −2° C., −3° C., −4° C., −5° C., −10° C., −15° C., −20° C., −30° C., −40° C., and −50° C. The cold slurry generated will have a plurality of sterile ice particles and will be suitable for injecting into a subject. Exemplary slurry compositions, slurry temperatures, and cross-sectional dimensions of ice particles are provided in International Application Publication No. WO/2016/033380, which is incorporated herein in its entirety. It is to be understood that an advantage of the cold slurry in accordance with the present invention is that the composition of the cold slurry is suitable for delivery to tissues within a patient's body and remain within the body (e.g. no removal of the slurry is necessary after cooling has been effected).

In one embodiment, the fluid contains one or more freezing point depressants, which depress the freezing point of the fluid, interfere with bonding between water molecules to prevent agglomeration of ice particles, alter the viscosity of the fluid or otherwise affect the performance of the fluid. Exemplary freezing point depressants are provided in International Application Publication No. WO/2016/033380, which is incorporated herein in its entirety, and include salts (e.g. sodium chloride), ions, Lactated Ringer's solution, sugars (e.g., glucose, sorbitol, mannitol, hetastarch, sucrose, or a combination thereof), biocompatible surfactants such as glycerol, other polyols, other sugar alcohols, and/or urea, and the like. In one aspect, the freezing point depressant content of the fluid is between about 5% and about 40%, between about 10% and about 30% or between about 12% and about 22%. In a preferred embodiment, the fluid includes a biocompatible surfactant such as glycerol. Such ingredients are believed to cause ice particles to shrink and become rounder. These ingredients can also serve as a cryo-protectant for non-lipid-rich cells.

In order to produce a cold slurry that selectively destructs lipid-rich cells while avoiding acute unselective necrosis, the slurry is preferably isotonic relative to the subject's cells, e.g., having an osmolarity of about 308 mOsm/L. An exemplary cold slurry composition includes normal saline and 20% glycerol. In non-selective, broader destructive slurries, colder temperatures and greater destructive power can be achieved by increasing the solute concentration (e.g., to 20% w/v saline) to form a hypertonic solution (i.e., a solution having an osmolarity greater than about 308 mOsm/L) that will also disrupt cells through osmotic pressure. It is noted that the solute concentration will decrease as the ice melts. It is also contemplated that the cold slurries can further include a therapeutic compound.

Furthermore, the cold slurries generated from the initial fluid can have varying ice contents, as provided in International Application Publication No. WO/2016/033380, which is incorporated herein by reference. For example but not limited to, the cold slurries can contain between about 0.1% and about 75% ice by weight, between about 0.1% and 1% ice by weight, between about 1% and 10% ice by weight, between about 10% and about 20% ice by weight, between about 20% and about 30% ice by weight, between about 30% and about 40% ice by weight, between about 40% and about 50% ice by weight, between about 50% and about 60% ice by weight, between about 60% and about 70% ice by weight, and greater than about 50% ice by weight. (The proportions of ice by volume are slightly higher due to the densities of solid and liquid water.)

The sterile ice particles can have a largest cross-sectional dimension that is less than about 2 mm, about 1.75 mm, about 1.5 mm, about 1.25 mm, about 1 mm, about 0.9 mm, about 0.8 mm, about 0.7 mm, about 0.6 mm, about 0.5 mm, about 0.4 mm, about 0.3 mm, about 0.2 mm or about 0.1 mm.

The fluid can contain additional excipients, such as those found in Sougata Pramanick et al., "Excipient Selection In Parenteral Formulation Development," 45(3) Pharma Times 65-77 (2013) and International Application Publication No. WO/2016/033380, both of which are incorporated herein by reference. Exemplary excipients include bulking agents, such as sucrose, lactose, trehalose, mannitol, sorbitol, glucose, raffinose, glycine, histidine, PVP (K40); buffering agents, such as sodium citrate, sodium phosphate, sodium hydroxide, tris base-65, tris acetate, tris HCl-65; tonicity modifiers, such as dextrose; collapse temperature modifiers such as dextran, ficoll, gelatin, and hydroxyethyl starch; antimicrobial preservatives, such as benzalkonium chloride, benzethonium chloride, benzyl alcohol, chlorobutanol, m-cresol, myristyl gamma-picolinium chloride, paraben methyl, paraben propyl, phenol, 2-phenoxyethanol, phenyl mercuric nitrate, and thimerosal; chelating agents, such as calcium disodium EDTA (ethylenediaminetetra acetic acid), disodium EDTA, calcium versetamide Na, calteridol, and DTPA; antioxidant and reducing agents, such as acetone sodium bisulfate, argon, ascorbyl palmitate, ascorbate (sodium/acid), bisulfite sodium, butylated hydroxyl anisole, butylated hydroxyl toluene (BHT), cystein/cysteinateHCl, dithionite sodium, gentistic acid, gentistic acid ethanolamine, glutamate monosodium, glutathione, formaldehyde sulfoxylate sodium, metabisulfite potassium, metabisulfite sodium, methionine, monothioglycerol (thioglycerol), nitrogen, propyl gallate, sulfite sodium, tocopherol alpha, alpha tocopherol hydrogen succinate, thioglycolate sodium, thiourea, and anhydrous stannous chloride; solvents and co-solvents, such as benzyl benzoate, oils, castor oil, cottonseed oil, N,N dimethylacetamide, ethanol, dehydrated ethanol, glycerin/glycerol, N-methyl-2-pyrrolidone, peanut oil, PEG, PEG 300, PEG 400, PEG 600, PEG 3350, PEG 4000, poppyseed oil, propylene glycol, safflower oil, sesame oil, soybean oil, vegetable oil, oleic acid, polyoxyethylene castor, sodium acetate-anhydrous, sodium carbonate-anhydrous, triethanolamine, and deoxycholate; buffers and pH-adjusting agents, such as acetate, ammonium sulfate, ammonium hydroxide, arginine, aspartic acid, benzene sulfonic acid, benzoate sodium/acid, bicarbonate-sodium, boric acid/sodium, carbonate/sodium, carbon dioxide, citrate, diethanolamine, glucono delta lactone, glycine/glycine HCl, histidine/histidine HCl, hydrochloric acid, hydrobromic acid, lysine (L), maleic acid, meglumine, methanesulfonic acid, monoethanolamine, phosphate (acid, monobasic potassium, dibasic potassium, monobasic sodium, dibasic sodium and tribasic sodium), sodium hydroxide, succinate sodium/disodium, sulfuric acid, tartarate sodium/acid, and tromethamine (Tris); stabilizers, such as aminoethyl sulfonic acid, asepsis sodium bicarbonate, L-cysteine, dietholamine, diethylenetriaminepentacetic acid, ferric chloride, albumin, hydrolyzed gelatin, insitol, and D,L-methionine; surfactants, such as polyoxyethylene sorbitan monooleate (TWEEN® 80), Sorbitan monooleate, polyoxyethylene sorbitan monolaurate (TWEEN® 20), lecithin, polyoxyethylene-polyoxypropylene copolymers (PLURONICS®), polyoxyethylene monolaurate, phosphatidylcholines, glyceryl fatty acid esters, urea; complexing/dispersing agents, such as cyclodextrins (e.g., hydroxypropyl-β-cyclodextrin, sulfobutylether-Bcyclodextrin); and viscosity building agents, such as sodium carboxymethyl cellulose, acacia, gelatin, methyl cellulose, polyvinyl and pyrrolidone.

The device 100 for generation and/or delivery of slurry is generally shown in FIG. 2. The delivery device 100 includes a cylindrical member 110 having a first (proximal) end 112, a second (distal) end 114; a longitudinal axis Y extending through the first end 112 and the second end 114; and an outer surface 116 extending between the first end 112 and the second end 114 along the longitudinal axis Y. The delivery device 100 also includes an interior lumen 130 defined by the interior wall of the cylindrical member 110. The interior lumen 130 receives and holds fluid to be cooled as well as the final cold slurry. The cylindrical member 110 also includes a ledge 150, or "arms", extending around the first end 112 out from the cylindrical member 110 along a plane that is orthogonal to the longitudinal axis Y. The ledge 150 also has an opening concentric with the interior lumen 130. The ledge 150 helps facilitate handling and delivery of fluid/slurry from the delivery device 100 and can also help secure the delivery device 100 within a cooling sleeve, the latter of which is described in more detail below.

In one embodiment, the delivery device 100 is a syringe-type device, such as a Type 91-3 syringe. The cylindrical member 110 can be made of any type of biocompatible pharmacologically inert material suitable for use in holding and supplying fluids to be provided within a human body. Exemplary materials for the cylindrical member 110 include plastic, such as polyethylene or polypropylene, and glass. The delivery device 100 can be any size that suitable to hold one or more aliquots or doses of cold slurry for delivery to the desired tissue. The volume capacity of the delivery device 100 is typically between 1 ml and 60 ml, although capacity outside of those volumes is also contemplated.

The delivery device 100 also includes a plunger 120 at least partially disposed within the interior lumen 130. The plunger 120 is configured to move in and out of the cylindrical member 110 along the longitudinal axis Y of delivery device 100 through the first end 112. The plunger 120 incudes, a head 122, a plunging member 124, and a rod 126. The rod 126 extends between the head 122 and the plunging member 124 along the longitudinal axis Y of the delivery device 100. The plunging member 124 is disposed at a predetermined distance from the head 122. The delivery device 100 also includes at least one needle 140 extending from the second end 114. The needle 140 will typically have a thickness between 7 gauge and 34 gauge and a length between ¼" and 10", such as about ¼", ½", 1", 2", 3", 4", 5", 6", 7", 8", 9" or 10". In one embodiment, the cylindrical member 110 narrows or tapers to a small opening at the second end 114. The small opening is configured to receive the needle 140. Preferably, the needle 140 is a hypodermic needle. Exemplary needle materials include, but are not limited to, stainless steel and carbon steel, with or without nickel plating.

In order for fluid to pass through the needle 140 without getting stuck or blocking flow of the cold slurry, the largest cross-section of the ice particles must be smaller than the internal diameter of the needle 140. For example, the largest cross section can be less than about 95% of the internal diameter, less than about 85% of the internal diameter, less than about 75% of the internal diameter, less than about 65% of the internal diameter, less than about 55%, and preferably about 50% of the internal diameter. Exemplary ice particle sizes for various internal diameters are provided in the table below, as disclosed in U.S. Patent Application Publication No. 2017/0274011, which is incorporated herein in its entirety. It is to be understood that these particles sizes are only meant to be exemplary and not for limitation.

| Needle Gauge | Nominal Internal Diameter | Recommended Largest Cross-Section of Ice Particles |
| --- | --- | --- |
| 7 | 3.81 mm | 1.905 mm |
| 8 | 3.429 mm | 1.7145 mm |
| 9 | 2.997 mm | 1.4985 mm |
| 10 | 2.692 mm | 1.346 mm |
| 11 | 2.388 mm | 1.194 mm |
| 12 | 2.159 mm | 1.0795 mm |
| 13 | 1.803 mm | 0.9015 mm |
| 14 | 1.6 mm | 0.8 mm |
| 15 | 1.372 mm | 0.686 mm |
| 16 | 1.194 mm | 0.597 mm |
| 17 | 1.067 mm | 0.5335 mm |
| 18 | 0.838 mm | 0.419 mm |
| 19 | 0.686 mm | 0.343 mm |
| 20 | 0.603 mm | 0.3015 mm |
| 21 | 0.514 mm | 0.257 mm |
| 22 | 0.413 mm | 0.2065 mm |
| 22s | 0.152 mm | 0.076 mm |
| 23 | 0.337 mm | 0.1685 mm |
| 24 | 0.311 mm | 0.1555 mm |
| 25 | 0.26 mm | 0.13 mm |
| 26 | 0.26 mm | 0.13 mm |
| 26s | 0.127 mm | 0.0635 mm |
| 27 | 0.21 mm | 0.105 mm |
| 28 | 0.184 mm | 0.092 mm |
| 29 | 0.184 mm | 0.092 mm |
| 30 | 0.159 mm | 0.0795 mm |
| 31 | 0.133 mm | 0.0665 mm |
| 32 | 0.108 mm | 0.054 mm |
| 33 | 0.108 mm | 0.054 mm |
| 34 | 0.0826 mm | 0.0413 mm |

Returning back to the cold slurry delivery device 100 of FIG. 2, the plunger 120, including the head 122 and the rod 126, can be any type of biocompatible, pharmacologically inert material suitable for coming in contact with fluids to be provided within a human body. Exemplary materials for the plunger 120 include plastic, such as polyethylene or polypropylene, and glass. With respect to the plunging member 124, a portion of or the entire plunging member 124 can be a rubber material, such that a seal is formed between the sides of the plunging member 124 and the interior wall of the cylindrical member 110. The rubber material can be any rubber suitable for coming in contact with fluids to be provided to the human body, such as natural rubber latex or a synthetic rubber.

During generation of the cold slurry within the interior lumen 130, the plunger 130 remains substantially in a stationary position with the plunging member 124 being located toward the first (proximal) end 112 of the cylindrical member 110, with the fluid being held between the plunging member 124 and the second (distal) end 114. In some aspects, the plunger 120 can be moved up through the cylindrical member 110, such that the plunging member 124 moves toward the first end 112 of the delivery device 100. Such movement creates a negative pressure on the fluid, which depresses the freezing point of the fluid.

Once the cold slurry has been generated and is ready for delivery to tissue using the delivery device 100, the needle 140 is used to pierce the patient's skin. Once the needle 140 is through the skin and positioned at or near the target tissue, the plunger 120 is forced downward toward the second end 114 of the cylindrical member 110. The force of the plunging member on the cold slurry, in conjunction with the increase in pressure of the cold slurry, forces the cold slurry through the cylindrical member 110 and out of the needle 140 into the tissue. In one aspect, a filter is provided within the cold slurry delivery device 100 at the second end 114 to help control the particle size of slurry ice particles that are delivered using the device 100.

Figure 3:
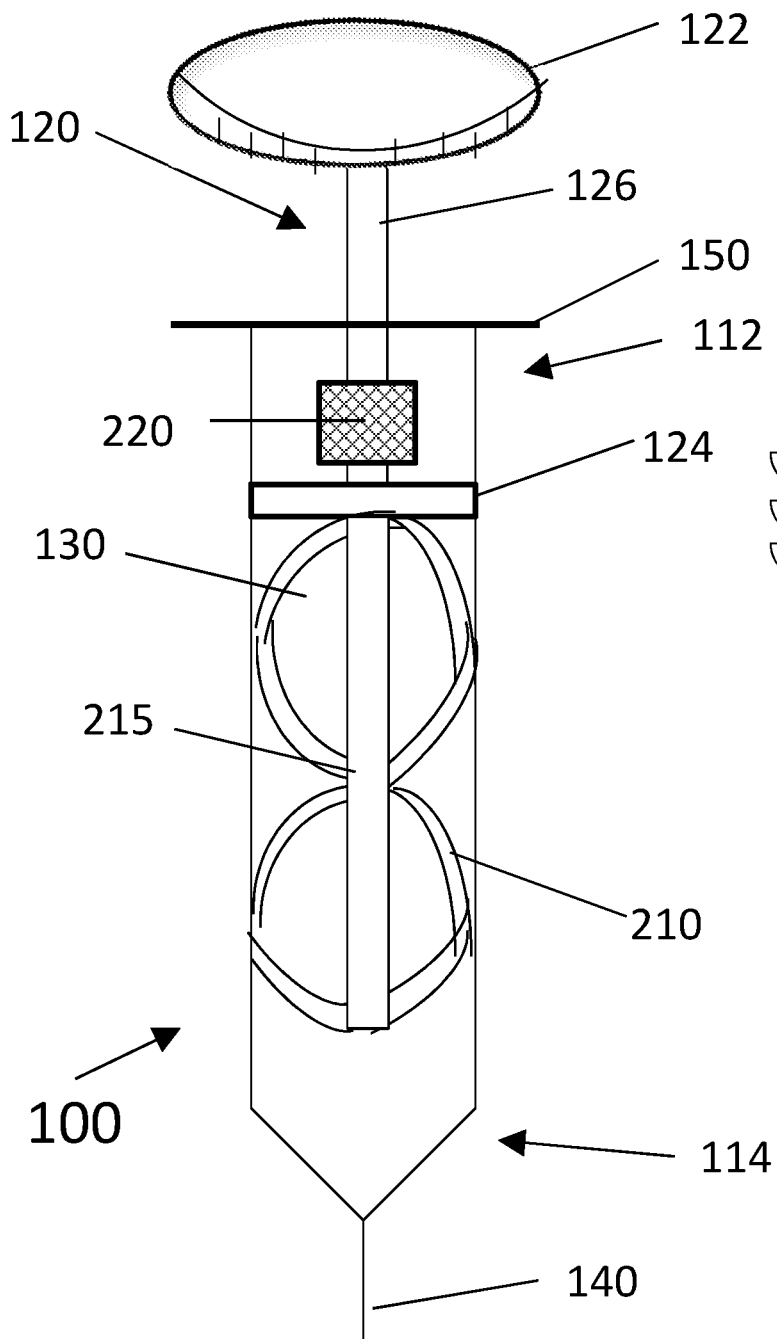
Figures 3A, 3B:
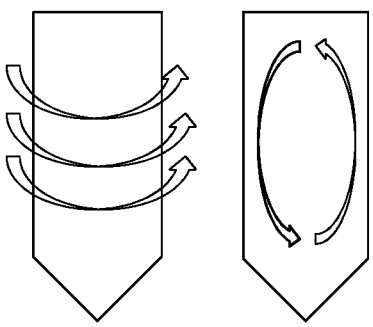
FIGS. 3A and 3B depict the movement of cold slurry within the apparatus according to the embodiment of FIG. 3.
Figure 3C:
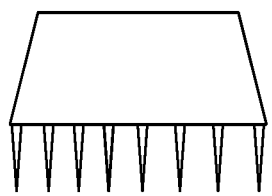
FIG. 3C shows a side view of a single array of needles of an example cold slurry delivery device.

In one embodiment, more than one needle is provided at the second end 114 of the delivery device 100, as shown in FIG. 3C. The more than one needles can be provided in single row array (as shown), multiple row array (not shown), circular pattern (not shown), or any other convenient arrangement.

To facilitate the formation of a cold slurry as the fluid is being cooled and/or to keep the sterile ice particles from aggregating as the cold slurry is being formed, agitation is provided within the cylindrical member 110. In one embodiment, agitation is provided through the rotation of one or more blades 210 and an optional support member 215 coupled to the plunger, as shown in FIG. 3. In one embodiment, the blades 210 are strips that allow fluid to flow between the blades 210 and the support member 215. In one aspect, the one or more blades 210 can crisscross each other to form a figure eight or similar pattern along the longitudinal axis. In another embodiment, the one or more blades 210 are solid in structure and extend out from the support member 215 toward the interior wall of the cylindrical member 110 in such a manner that fluid is not able to flow between the support member 215 and the blades 210. The blades 210 can extend out from the support member 215 along a plane wherein one dimension of the plane is defined by the longitudinal axis Y of the cold slurry delivery device 100. Alternatively, the blades 210 can extend out from the support member 215 along a plane that intersects the longitudinal axis at an angle. The blades 210 can be made out of any material that is suitable for contact with sterile compositions to be delivered to the human body, including those exemplary materials previously provided with respect to the cylindrical member 110, plunger 120, and needle 140.

Figures 4A, 4B:
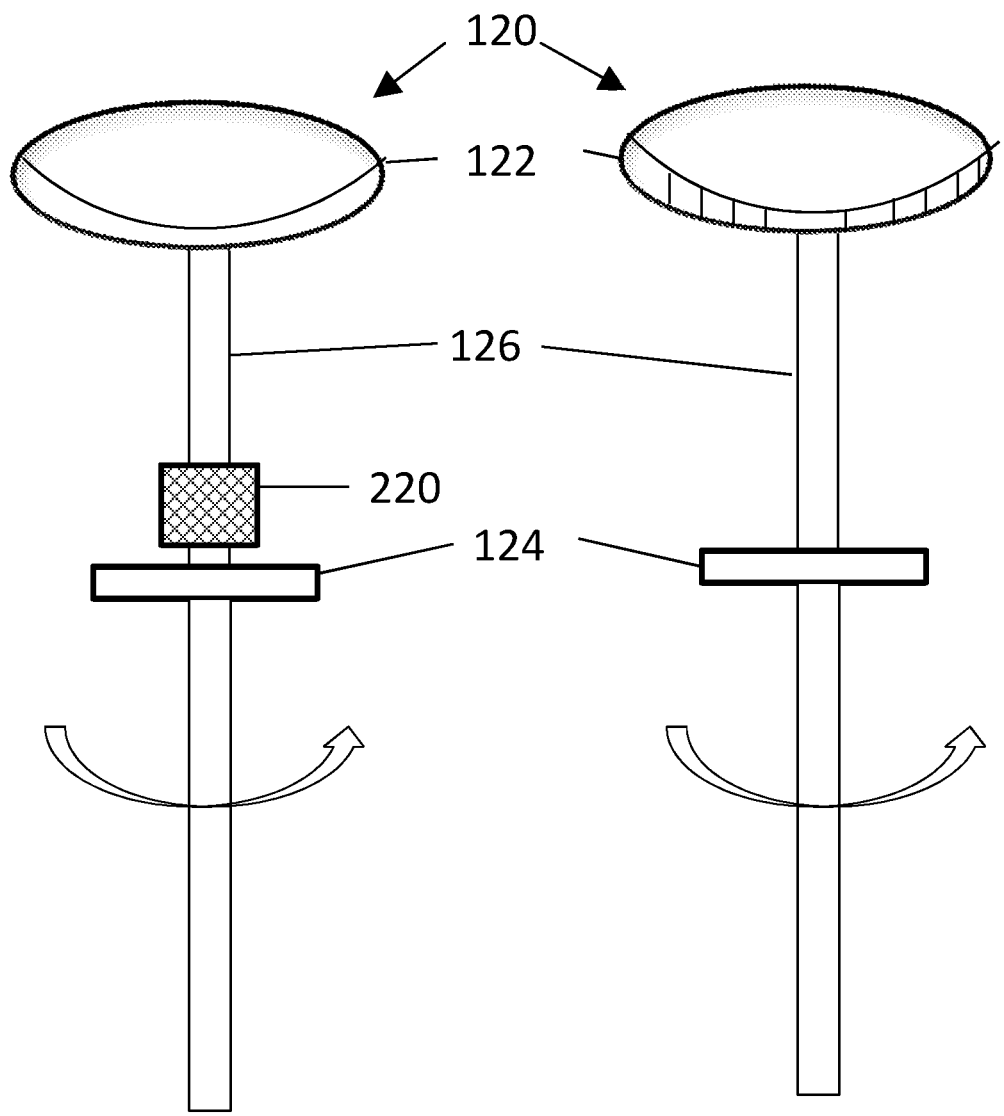
FIGS. 4A and 4B depict the different embodiments for placement of a motor that effects rotation.

In one embodiment, the rotation of the plunger 120 causes rotation of the blades 210, which in turn causes the fluid/slurry to flow in multiple directions, as shown in FIGS. 3A and 3B. In one embodiment, rotation of the plunger 120 is done manually by turning the plunger head 122 using one's hand or a crank. In another embodiment, rotation is aided with the use of a motor 220. The motor can be coupled to the cold slurry delivery device 100 in any number of positions. For example, in one embodiment, the motor 220 is coupled to the plunger 120 along the rod 126, as shown in FIG. 4A, with the rod 126 acting as a gear. In one aspect, the motor 220 is coupled to the rod 126 between the head 122 and the plunging member 124. In another embodiment shown in FIG. 4B, the motor 220 is coupled to the plunger 120 through the plunger head 122, which acts as a gear. In another aspect, the blades 210 are collapsible and/or flexible, such that when force is applied to the plunger 120 and the plunging member 124 is moved towards the second end 114, the blades 210 collapse allowing the plunger 120 to travel through the cylindrical member 110 and force the cold slurry out of the cold slurry delivery device 100.

Figure 5:
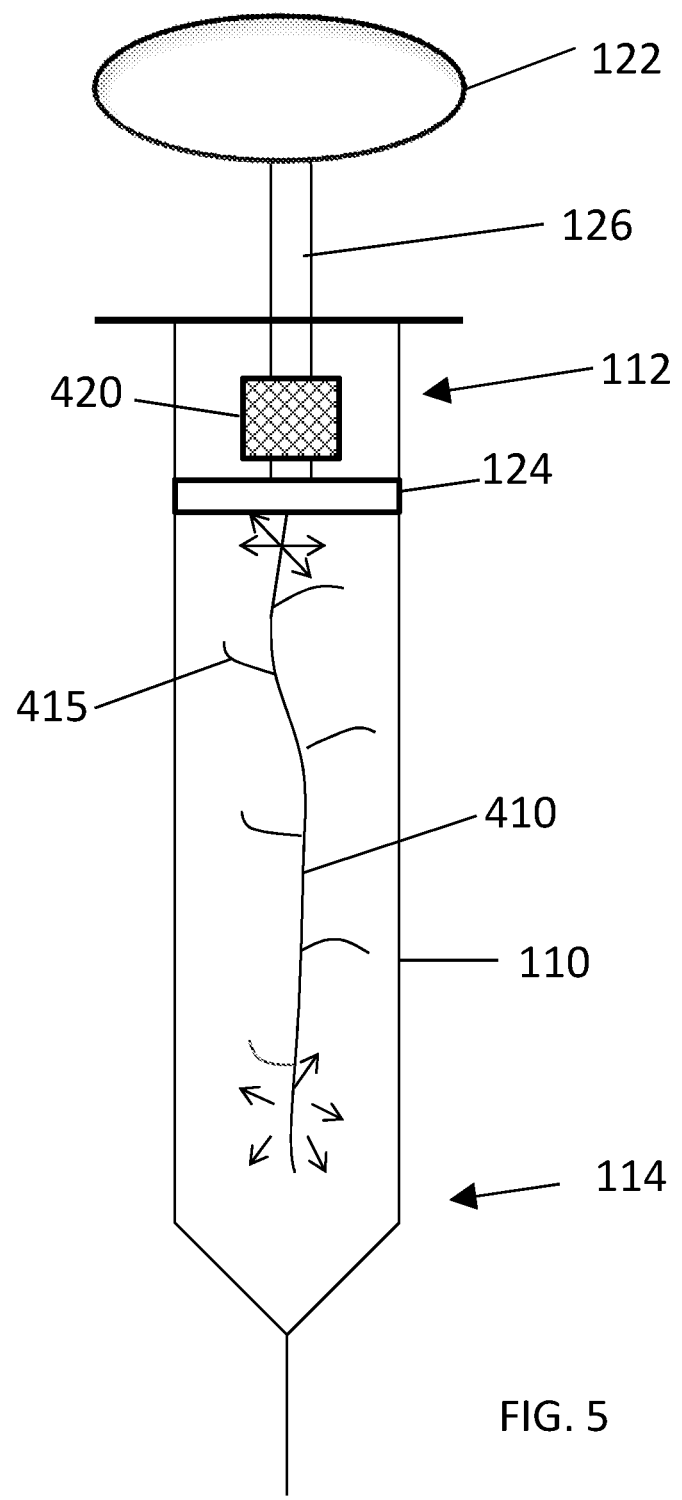
FIG. 5 shows a perspective view of a cold slurry delivery apparatus with an agitation device in accordance with another embodiment of the present invention.

In another embodiment, as shown in FIG. 5, agitation is provided through the use of vibration. In this embodiment, a wire 410 extends from the plunging member 124 toward the second end 114 of the cylindrical member 110, along the longitudinal axis Y of the cold slurry delivery device 100. Vibration is provided to the wire 410 by a motor 420, such as a battery powered vibrational motor, coupled to the plunger 120. When vibration is provided to the wire 410, the wire 410 moves in a number of directions (as depicted in the figure by the arrows) to provide agitation to the fluid/slurry. In one aspect, one or more wire tentacles 415 can be provided along the wire 410, which extend out from the wire 410 and toward the inside wall of the cylindrical member 110. The tentacles 415 provide additional vibration and motion. Similar to the other components provided within the cold slurry delivery device 100, the wire 410 and tentacles 415 can be made of any material that is biocompatible and pharmacologically inert.

It is to be understood that any other means known in the art to agitate a fluid can be used to provide agitation during generation of the cold slurry.

Figures 6, 6A:
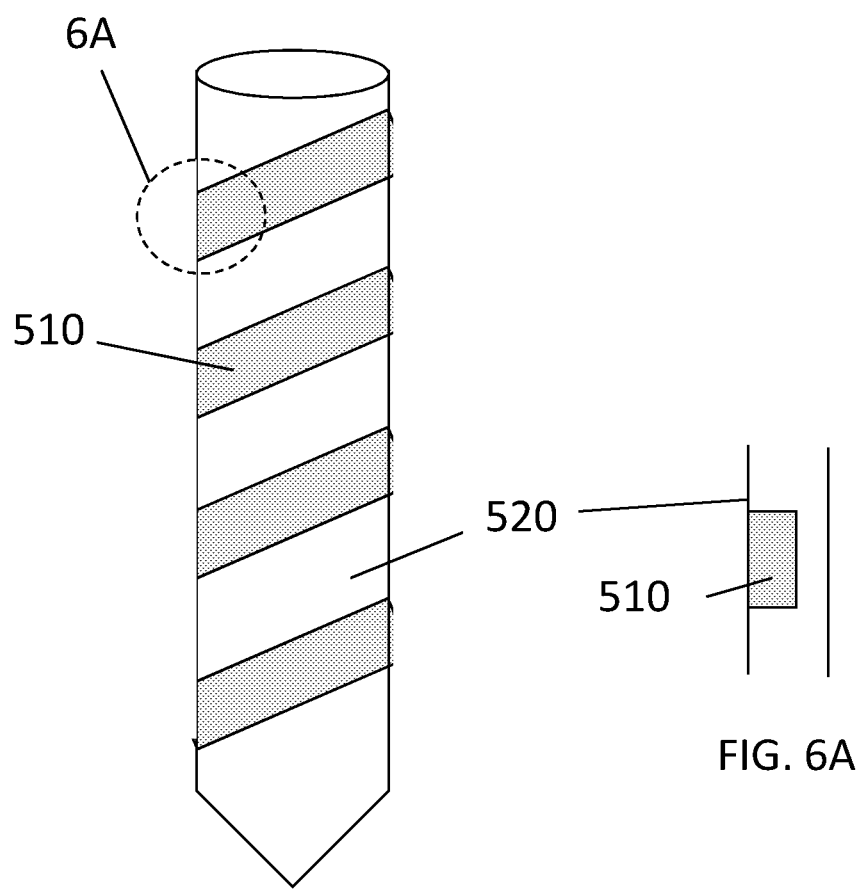
FIG. 6 depicts a cold slurry delivery apparatus having a conductive material on its outer surface and FIG. 6A depicts a cross section of the wall of the apparatus showing the conductive material embedded in wall.

In order to effectuate the transfer of heat away from the cold slurry/transfer of cold to the cold slurry, the cold slurry delivery device 100 can be provided with a conductive material. In one embodiment, as shown in FIGS. 6 and 6A, a conductive material 510 is provided to the outer surface 116 of the cold slurry delivery device 100. The conductive material 510 can be provided to the outer surface 116 through a sheath 520 that surrounds the outer surface 116 of the cylindrical member 110. In one aspect, the conductive material is provided as an inlay on the outer surface of the sheath 520. The inlay can be disposed about the sheath 520, such that the inlay does not extend the entire depth of the sheath wall, as shown in FIG. 6A.

Alternatively or additionally, the cylindrical member 110 itself comprises a conductive material 510. In one aspect, the conductive material 510 is provided throughout the walls of the cylindrical member 110. In another aspect, the conductive material 510 is provided to the outer surface 116 of the cylindrical member 110 as an inlay. In yet another aspect, the conductive material 510 is provided to the cylindrical member 110, such that the inlay is in contact with the fluid contained within the interior lumen 130 of the cylindrical member 110.

The conductive material 510 can be any material capable of effecting heat transfer. Exemplary conductive materials include, but are not limited to, silver, copper, gold, aluminum, brass, zinc, nickel, iron, tin, phosphor bronze, steel, and lead. In a preferred embodiment, the conductive material 510 comprises copper.

The conductive material 510 can be provided on about 5% to about 95% of the surface of the sheath 520 and/or the cylindrical member 110, such as on about 5%, 10%, 15%, 20%, 25%, 30%, 40%, 50%, 60%, 70%, 75%, 80%, 90%, 95%, 100% or another other percentage in-between. In one aspect, the conductive material 510 is provided as strips that wrap around the sheath 520 and/or the cylindrical member 110. However, it is to be understood that the conductive material can be disposed on the sheath/cylindrical member 110 in any manner.

Figure 7:
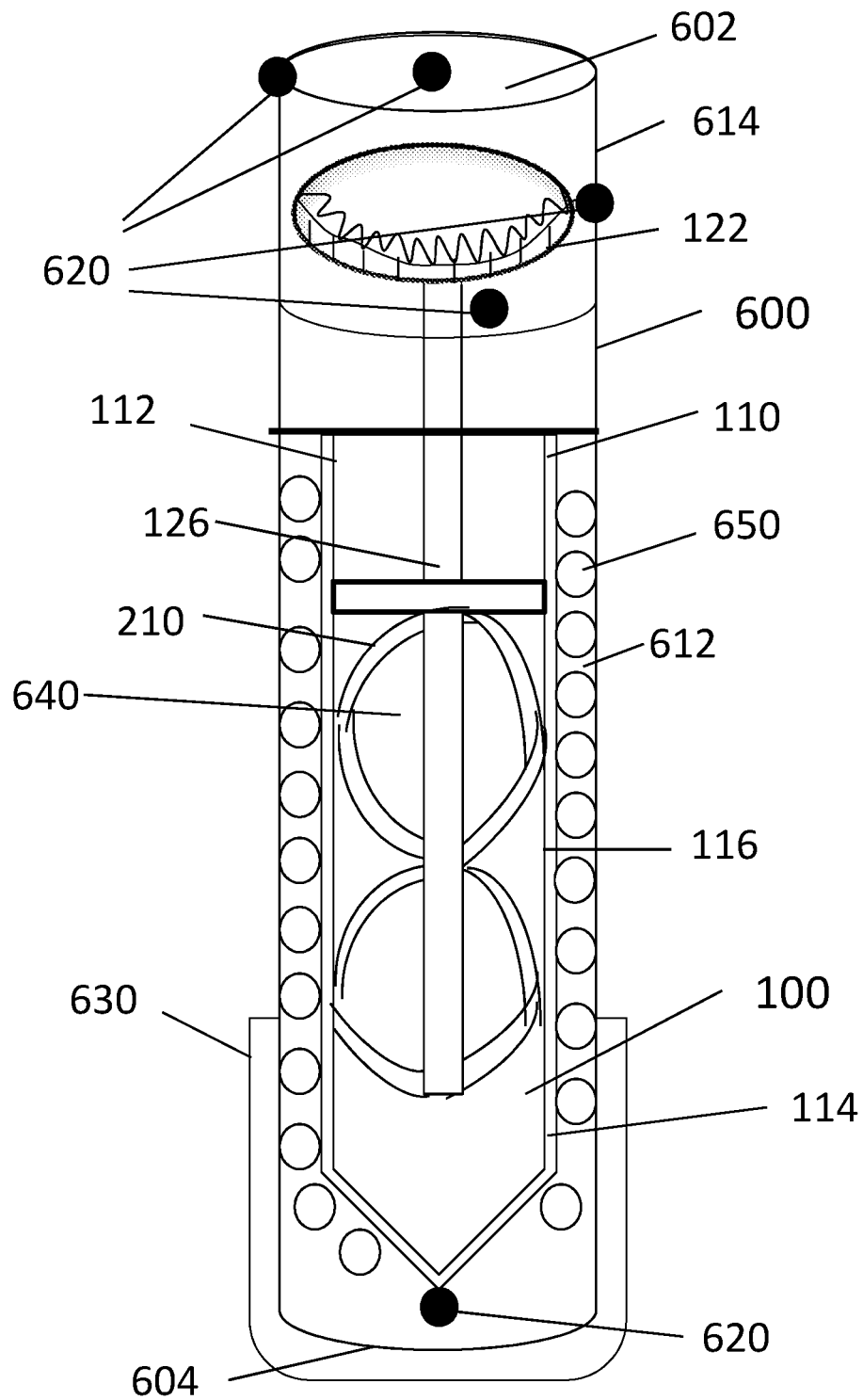
FIG. 7 depicts a cross sectional perspective view of a cold slurry delivery apparatus with a cooling sleeve according to an embodiment of the present invention.

In one embodiment according to the present invention shown in FIG. 7, the apparatus also includes a cooling sleeve 600 that surrounds the cylindrical member 110 and cools or maintains a temperature of the cold slurry within the interior lumen 130. The cooling sleeve 600 can provide cooling through any number of mechanisms, such as through the use of circulating refrigerant, the use of an endothermic reaction, and the use of pressure.

The cooling sleeve 600 is concentric with the outer surface 116 of the cylindrical member 110 and is spaced apart from the outer surface 116, such that a space 612 is formed between the cooling sleeve 600 and the cylindrical member 110. In one embodiment, the cooling sleeve 600 is configured to provide an interior chamber 640 for receiving the cold slurry delivery device 100. In one aspect, the cooling sleeve 600 has a bottom 604 that extends below the second end 114 of the cylindrical member 110 and a top 602 that extends above the first end 112 of the cylindrical member 110 and the plunger head 122, such that the cooling sleeve 600 encompasses the cold slurry delivery device 100 in its entirety, as shown in FIG. 7. A removable cap 614 is provided at the top 602 of the cooling sleeve 600 to allow for insertion and subsequent enclosure of the cold slurry delivery device 100 within the cooling sleeve 600. Similar to the components of the cold slurry delivery device 100, the cooling sleeve 600 can be made out of any material that is biocompatible and pharmacologically inert. However, because the cooling sleeve 600 may not come in contact with the fluid contained within the cold slurry delivery device 100, additional materials can be used.

In one embodiment in which rotation is used to agitate the fluid within the cold slurry delivery device 100, a motor 620 and associated gear can be disposed on/coupled to the device 100, such as on the plunger head 122 or rod 126, as disclosed previously and as shown in FIG. 7. The motor 620 and associated gear can also be disposed on/coupled to the cooling sleeve 100, such as on the cap 614 along the longitudinal axis or around the top edge of the cap 614, the edge is being provided with gear teeth, as also shown in FIG. 7. The motor 620 can also be disposed on/coupled to the cooling sleeve 600 at the second end 114 of the cylindrical member 110. It is also to be understood that the motor 620 and associated gear can be disposed at any other location within or on the cold slurry delivery device 100 or the cooling sleeve 600 that facilitates rotation and is not limited to the examples provided above and that the gear teeth can be located inside or outside one or both of the cooling sleeve 600 and the cold slurry delivery device 100.

In one embodiment in which cooling via the cooling sleeve 600 is effected through the use of a circulating refrigerant, at least one tubular member 650 is provided within the space 612 between the cooling sleeve 600 and the cylindrical member 110, as shown in FIG. 7. The tubular member 650 is disposed axially about the outer surface 116 of the cylindrical member 110, with the tubular member 650 extending at least partially around a circumference of the outer surface 116. In a preferred embodiment, the tubular member 650 is wrapped around the cylindrical member 110 to form a coil. The tubular member 650 is hollow to allow for cooling fluid to flow through its interior.

In one aspect, a cooling fluid supply unit 630 is provided to the cooling sleeve 600 for supplying the cooling fluid to the cooling sleeve 600. In one embodiment, the cooling fluid supply unit 630 surrounds at least a portion of the cooling sleeve 630, including the bottom 604 of the cooling sleeve 600, as shown in FIG. 7. The cooling fluid supply unit 630 is fluidically connected to the tubular member 650 in order to supply cooling fluid to the tubular member 650. In one embodiment, the cooling fluid supply unit 630 is similar to a circuit chiller, which provides a stream of cooling fluid upon the depression of a trigger.

The cooling fluid can be any fluid capable of providing cooling. In one embodiment, the cooling fluid is a commercially available refrigerant, such as Ammonia (R717), HCF (134a/R-134a), $CO_2$ (R-744), and HFO-1234yf (2,3,3,3-Tetrafluoropropene) or others, such as R404A, R407A, R744, R290, and R410A. In another embodiment, the cooling fluid is liquid nitrogen.

Figure 8:
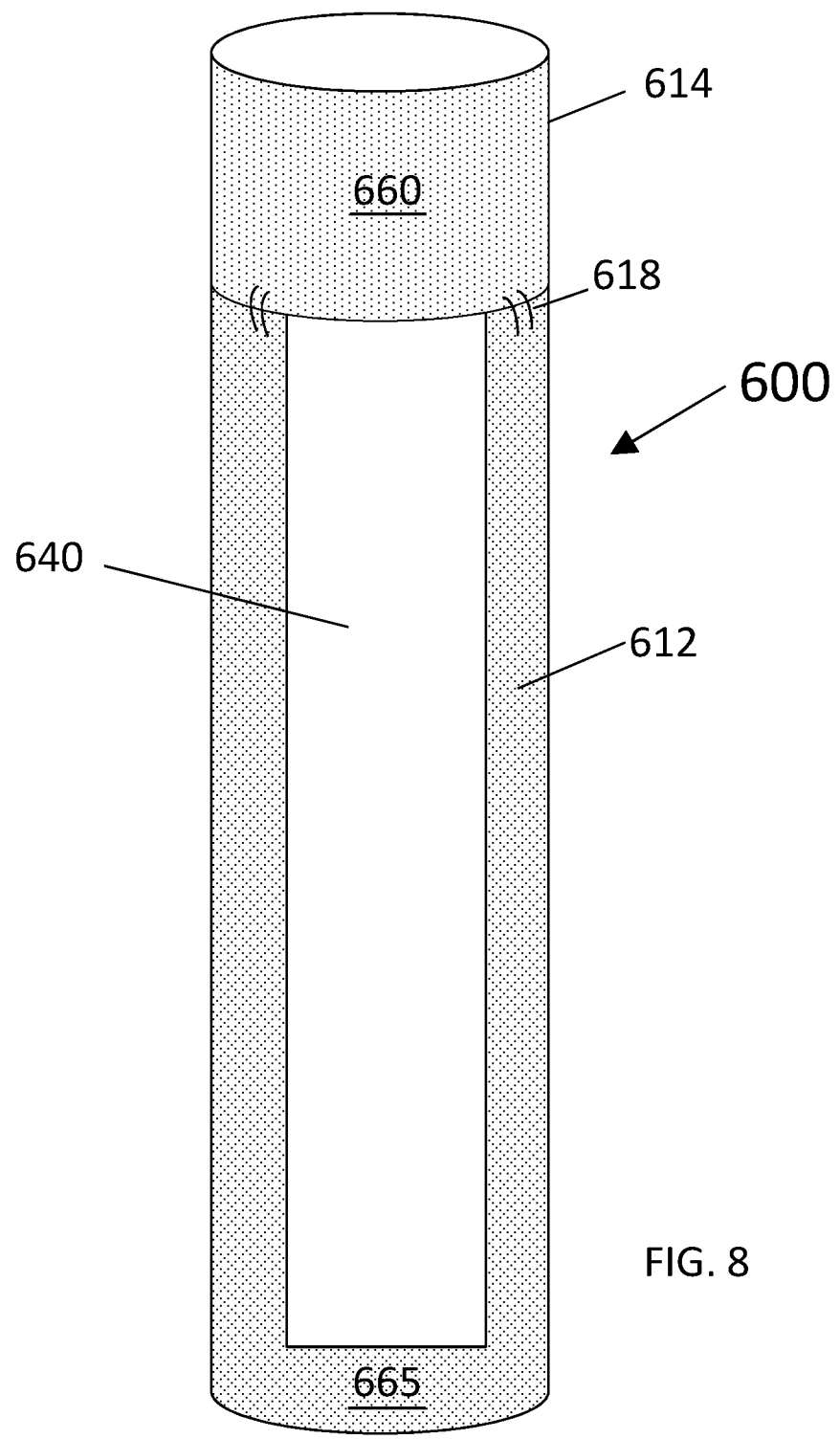
FIG. 8 depicts a cross sectional perspective view of a cold slurry delivery apparatus with a cooling sleeve according to another embodiment of the present invention.

The cooling sleeve 600 can also provide cooling through the use of an endothermic reaction, as shown in FIG. 8. In this embodiment, a first chemical 660 is provided within an interior space of the cap 614 of the cooling sleeve 600 and a second chemical 665 is provided within the space 612 between the cooling sleeve 600 and the cylindrical member 110 (not shown).

The first and second chemicals 660, 665 are chosen such that the mixture of the two chemicals within the space 612 between the cooling sleeve 600 and the outer surface 116 of the cylindrical member 110 produces an endothermic reaction, thus providing cooling to the cold slurry delivery device within a chamber 640. Exemplary combinations of chemicals that produce an endothermic reaction include, but are not limited to the following: ammonium thiocyanate and barium hydroxide octahydrate; water and sodium thiosulphate; water and ammonium chloride; water and ammonium nitrate; and water and potassium nitrate.

A seal 618 is provided between the cap 614 and the remainder of the cooling sleeve 600 to prevent the first chemical 660 and the second chemical 665 from mixing with each other until cooling is desired. The seal 618 can be broken by any means known in the art, such as by twisting the cap 614 to break the seal 618. Once the seal 618 is broken, the first chemical 660 is released from the cap 614 and enters the space 612 and mixes with the second chemical 665 to provide an endothermic reaction.

Figures 9, 9A:
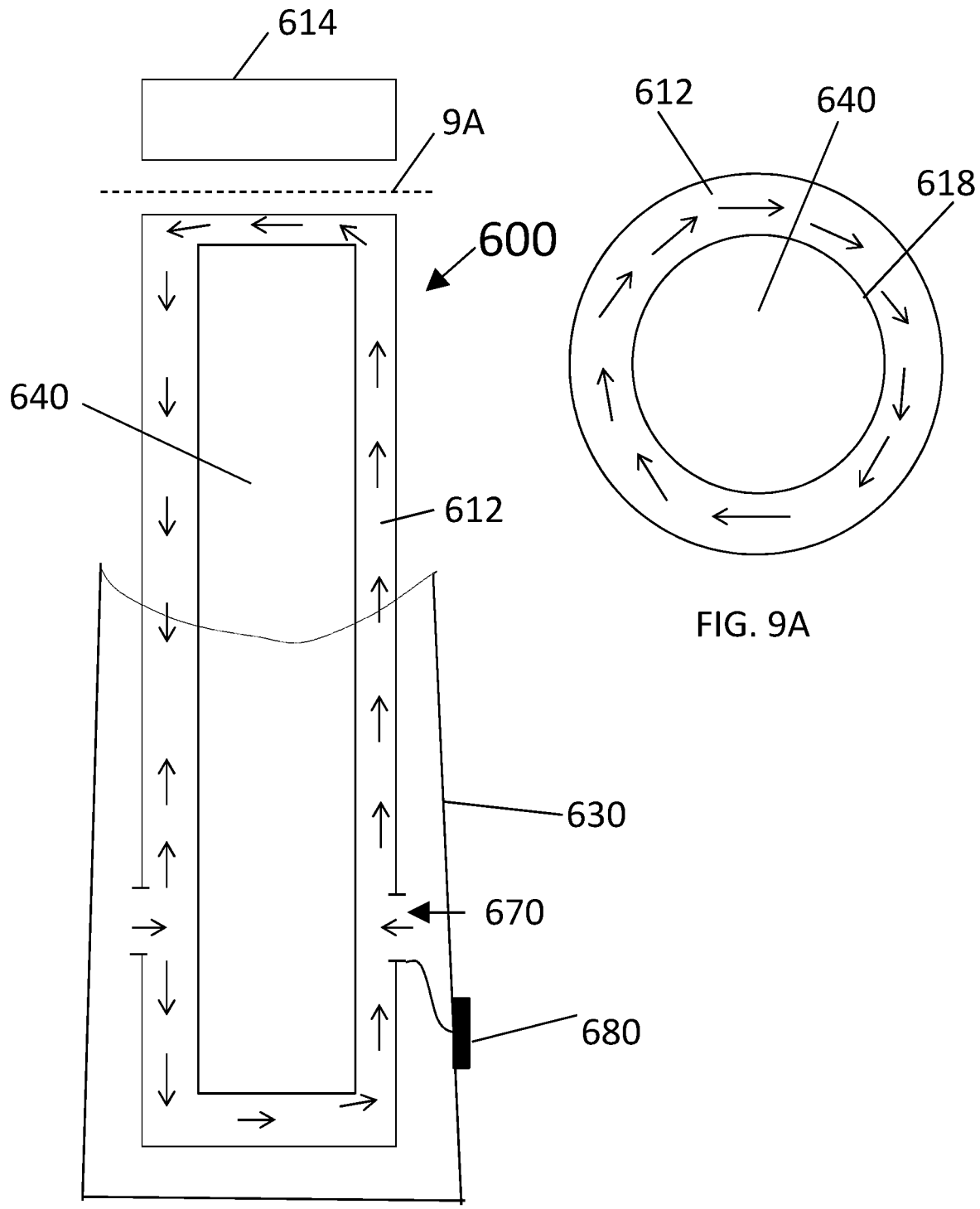
FIG. 9 depicts a cross sectional exploded perspective view of a cold slurry delivery apparatus with a cooling sleeve according to another embodiment of the present invention and FIG. 9A depicts a top-down cross sectional view taken at line 9A.

The cooling sleeve 600 can also provide cooling through the use of a cooling fluid that circulates through the space 612 between the cylindrical member 110 and the cooling sleeve 600, as shown in FIG. 9. In this embodiment, the space 612 forms a chamber for holding and circulating a fluid, preferably a cooling fluid.

Similar to the embodiment featured in FIG. 7, the cooling fluid can be any fluid capable of providing cooling. In one embodiment, the cooling fluid is a commercially available refrigerant, such as Ammonia (R717), HCF (134a/R-134a), $CO_2$ (R-744), and HFO-1234yf (2,3,3,3-Tetrafluoropropene) or others, such as R404A, R407A, R744, R290, and R410A. In another embodiment, the cooling fluid is liquid nitrogen.

In one aspect, the cooling fluid is provided to the cooling sleeve 600 via the cooling fluid supply unit 630 that surrounds at least a portion of the cooling sleeve 600. The cooling fluid can be released from the container and into the space 612 through one or more inlets 670 (or valves). The inlets 670 remain closed until triggered by a signal from a release mechanism 680. Once triggered by the signal, the one or more inlets 670 will open and allow passage of the cooling fluid from the cooling fluid supply unit 630 and into the space 612. Fluid flows through the space 612 in a direction parallel to the longitudinal axis, as shown in FIG. 9, as well as in an circular direction, as shown in the top-down cross-sectional view of FIG. 9A, which is taken at line 9A.

In another aspect, a conductive membrane 618 is provided between the space 612 and the chamber 640, as shown in FIG. 9A, such that the conductive membrane 618 interacts with the conductive material 510 provided on at least the outer surface of the cold slurry delivery device 100. Similar to the conductive material 510, the conductive membrane 618 can be any material capable of effecting heat transfer. Exemplary conductive membrane materials include, but are not limited to, silver, copper, gold, aluminum, brass, zinc, nickel, iron, tin, phosphor bronze, steel, and lead. In a preferred embodiment, the conductive membrane 618 comprises copper.

Figure 10:
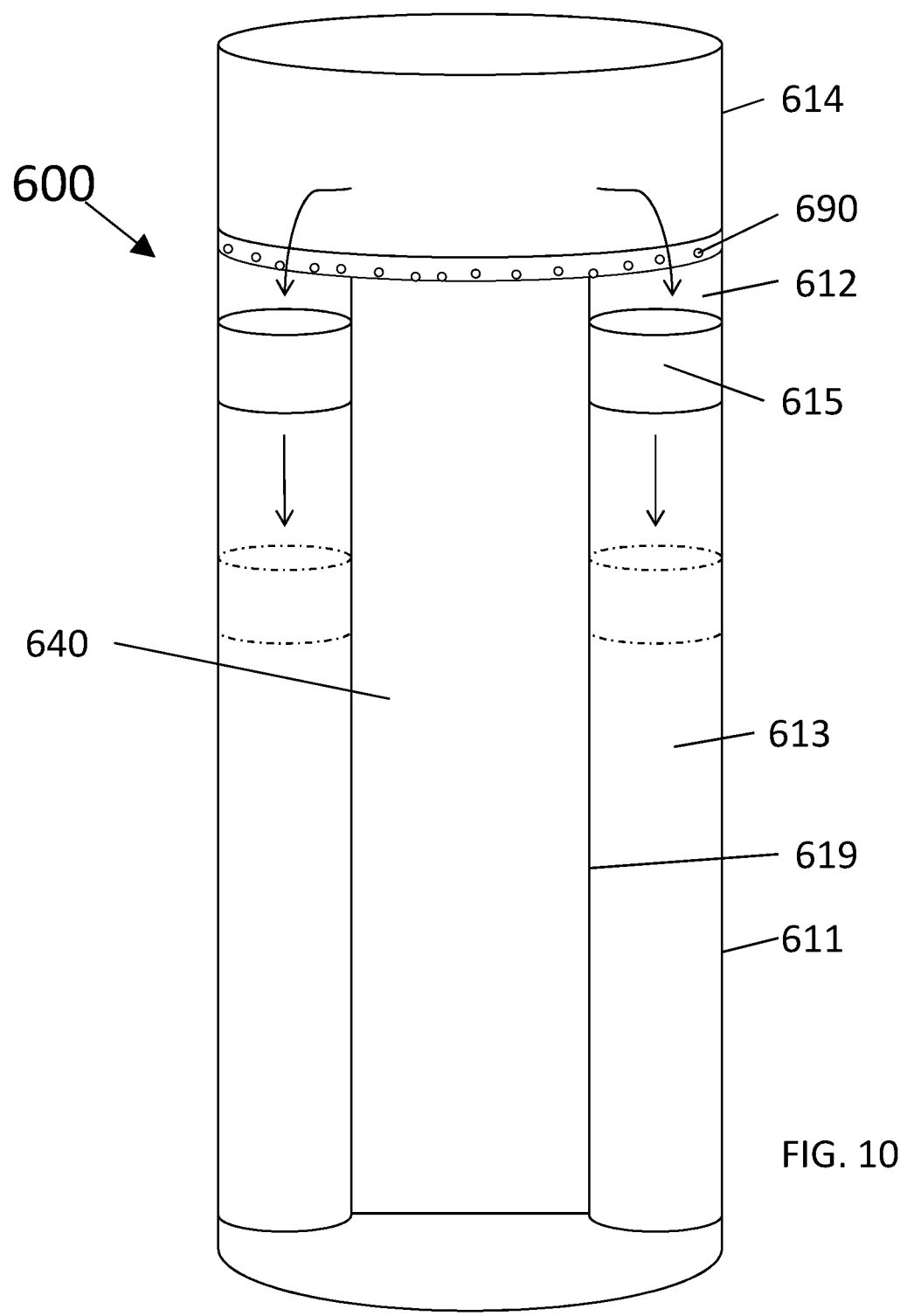
FIG. 10 depicts a cross sectional perspective view of a cold slurry delivery apparatus with a cooling sleeve according to another embodiment of the present invention.

The cooling sleeve 600 can also provide cooling through the use of pressure to lower the temperature, as shown in FIG. 10. In this embodiment, at least one chamber 613 is disposed within the space 612. The at least one chamber 613 extends along a second axis parallel to the longitudinal axis. In one aspect the chamber 613 is cylindrical in shape. The chamber 613 contains a fluid to be compressed. Any number of chambers can be provided within the space 612, such as 1, 2, 3, 4, 5, 6, 7, 8, 9, 10, 15, 20, 25, and any number in between.

Pressurized gas for compressing the fluid in the one or more chambers 613 is provided within the cap 614, with the cap 614 forming a high pressure gas chamber. In one aspect, a plunger 615 is provided within the chamber 613. When cooling is desired, the compressed gas is released from the cap 614 via gas release mechanism 690. The compressed gas pushes downward on the plunger 615, thus activating the plunger 615 to compress the fluid. The rapid compression of fluid creates rapid cooling to the chamber 640, thus cooling and/or maintaining the cold temperature of the fluid/slurry within the cold slurry delivery device 100 being held within the chamber 640.

In one aspect of this embodiment, at least a portion of a wall of the chamber 613 that faces the cylindrical member 110 comprises a conductive membrane for interacting with the conductive material 510 to assist in the transfer of heat. At least a portion of the chamber wall that faces away from the cylindrical member 110 comprises a thick membrane 611.

Figures 11A, 11B:
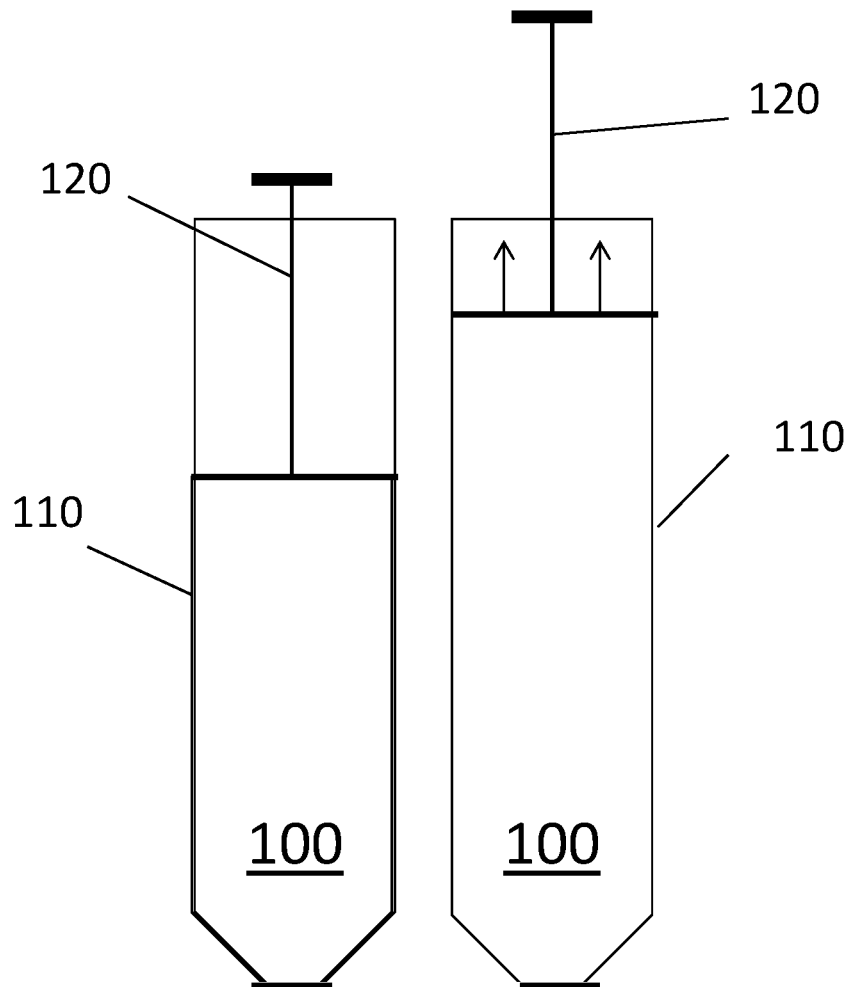
FIGS. 11A and 11B depict the creation of negative pressure on the fluid contained within the cold slurry delivery device through the use of the plunger.

Additionally, during generation of the cold slurry using any of the apparatuses and devices described above, the plunger 120 can be used to create a negative pressure on the fluid to effect a decrease in the freezing temperature of the fluid. An example of this is shown in FIGS. 11A and 11B. The plunger 120 in 11A is shown prior to being drawn upwards toward the first end 112 of the cold slurry delivery device 100, while the plunger 120 in 11B is being drawn upwards toward the first end 112 of the cold slurry delivery device 100 to create negative pressure on the fluid. Accordingly, the pressure on the fluid is lower in 11B than it is in 11A.

In accordance with another embodiment of the present invention, cold slurry can be generated in a separate chamber, a slurry generation chamber 300, using a cooling source and an injectable fluid, optionally with the aid of a solid salt water source. In one aspect, the volume of the slurry generation chamber 300 is less than about 1 L, such as less than about 800 ml, less than about 700 ml, less than about 600 ml, less than about 500 ml, less than about 400 ml, less than about 300 ml, less than about 200 ml, less than about 100 ml, less than about 90 ml, less than about 80 ml, less than about 70 ml, less than about 60 ml, less than about 50 ml, less than about 25 ml, and less than about 10 ml.

Figures 12, 12A:
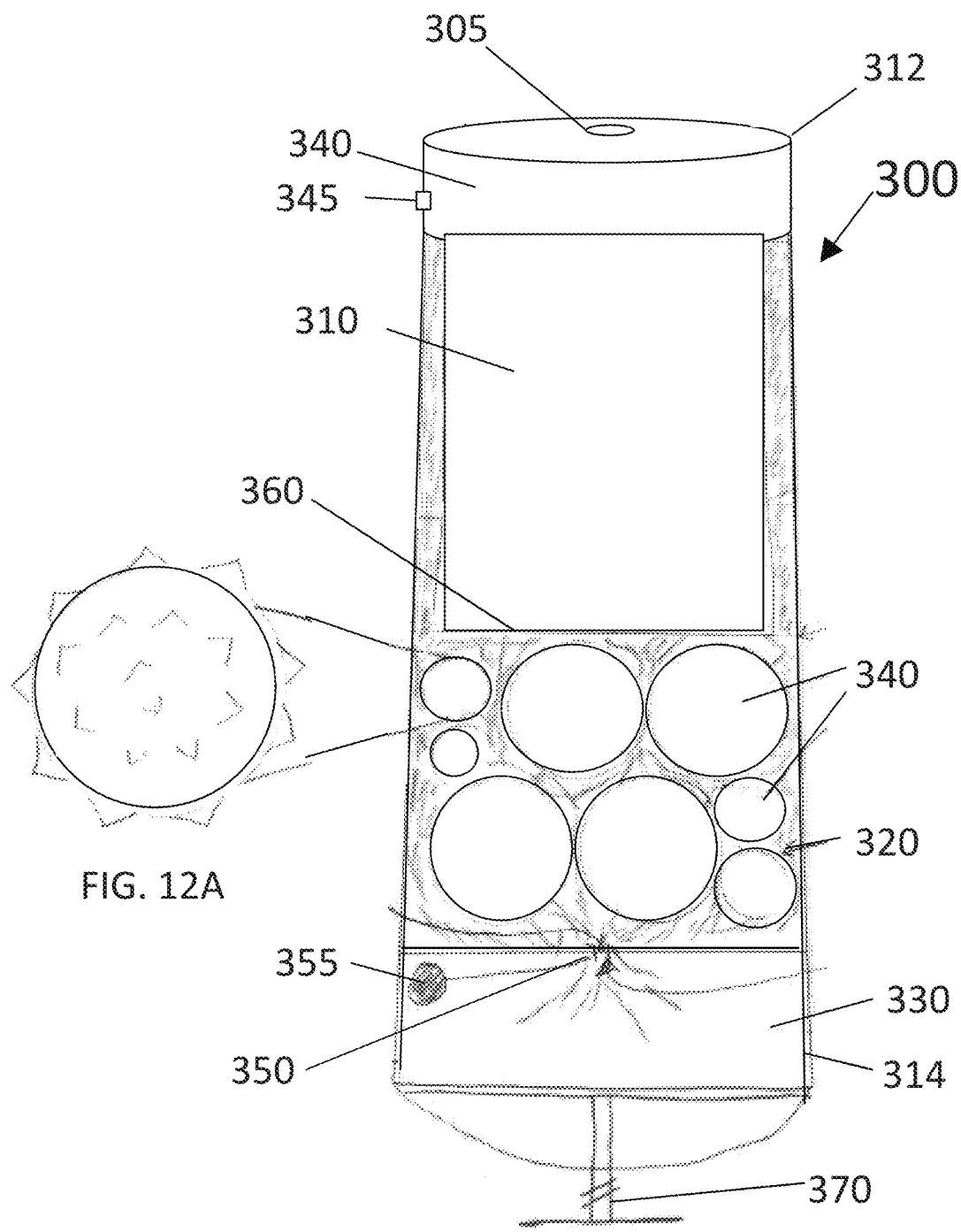
FIG. 12 depicts a cross sectional perspective view of the slurry generation chamber in accordance with an embodiment of the invention and FIG. 12A shows a close up view of a solid salt water filled sphere of FIG. 12.

The slurry generation chamber 300, as shown in FIG. 12, has a top end 312 and a bottom end 314. The top end 312 contains a connector 305. In one aspect, the slurry generation chamber 300 is divided into at least 3 compartments. A first compartment 310 holds an injectable fluid that is suitable for injection into a patient's body. The injectable fluid can comprise salt, sugar, and/or any other pharmaceutically acceptable excipient provided above. The first compartment 310 can comprise a rigid housing or can be flexible, such that a vacuum is formed when fluid is ejected from the first compartment 310. In the case that a vacuum is formed, vapor may be created. Accordingly, the slurry generation chamber 300 also includes an air space 340 for vapor located towards the top end 312 of the chamber 300. In one aspect, a vapor release valve 345 is also provided.

A second compartment 320 can initially be empty or can comprise a solid salt water source. In one embodiment, the solid salt water source is a plurality of salt water filled particles 340. The particles 340 can be any shape, such as spherical, cylindrical, torus-shaped, conical, square, elliptical, etc. It is to be understood that the particles 340 do not have to be perfectly shaped and instead can include imperfections and oddities. In one embodiment, the particles 340 are substantially spherical. In another embodiment, the particles 340 have nodules or bumps on the outer surface, as shown in FIG. 12. The nodules act to increase the surface area available for interaction. The nodules also provide additional agitation and ability to separate the particles 340 from one another.

The first compartment 310 and the second compartment 320 are separated from one another through a separation member 360. The separation member 360 can comprise one or more valves that can be opened upon reaching a certain pressure or upon receipt of a signal from a release trigger operatively coupled to the separation member 360. Alternatively, the separation member 360 can comprise a breakable seal that is broken by twisting a portion of the slurry generation chamber 300 or through the use of a trigger. Once the separation member 360 has been breached, the fluid from the first compartment 310 and fluid and/or salt water filled particles 340 contained in the second compartment 320 will mix together.

A third compartment 330 comprises a cooling fluid, the cooling fluid being safe for delivery within the patient's body. In a preferred embodiment, the cooling fluid is compressed within the third compartment 330. Exemplary cooling fluids include liquid nitrogen, HCF-134A, and other refrigerants which are deemed acceptable for use by the Environmental Protection Agency and government entities. Preferably, the cooling fluid is safe for humans.

The third compartment 330 is in fluid communication with the second compartment 320 through one or more valves 350. In one embodiment, the valve 350 is set to open at a predetermined pressure. In another embodiment, the valve 350 is opened upon receipt of a signal from a release trigger 355 that is operatively coupled to the valve 350. In one aspect, the valve 350 is a one-way valve, such that fluid only flows through the valve 350 in a direction from the third compartment 330 to the second compartment 320.

Preferably, the contents of the three compartments (310, 320, and 330) are kept separate from each other until just prior to delivery of the cold slurry at the point of care. Keeping the compartments separate ensures that the cold slurry is not generated until desired. In this way, the slurry generation chamber 300 can be manufactured in mass at a separate facility and shipped without requiring refrigeration; the only action needed to generate a cold slurry at the point of care is the activation of the release trigger 355 and the shaking of the slurry generation chamber 300.

In one particular embodiment, as shown in FIG. 12, in one embodiment, the first compartment 310 is provided toward the top end 312 of the slurry generation chamber 300, the third compartment 330 is provided toward the bottom end 314 of the slurry generation chamber 300, with the majority of the second compartment 320 located between the first compartment 310 and the third compartment 330. In one aspect of the embodiment, a portion of the second compartment 320 surrounds the first compartment 310, such that the second compartment 320 is provided between the first compartment 310 and the wall of the slurry generation chamber 300.

In operation, the opening of the valve 350 releases cooling fluid from the third compartment 330 and into the second compartment 320. The cooling fluid interacts with the salt water filled particles 340, lowering the temperature of the particles 340 to a desired temperature. The cooling fluid will also lower the temperature of the injectable fluid contained within the first compartment 310 as the cooling fluid flows into the second compartment 320.

Once the salt water filled particles 340 have been chilled to a desirable temperature, intentional breach of the separation member 360 occurs, such that the particles 340 and the injectable fluid comingle. The chilled salt water filled particles 340 continue to lower the temperature of the injectable fluid, such that a cold slurry is eventually formed. The chilled salt water filled particles 340 also serve to agitate and separate the ice crystals forming in the cold slurry as the temperature drops. Additionally, the slurry generation chamber 300 is subject to further agitation, such as by shaking the slurry generation chamber 300, with the additional agitation assisting in the cold slurry formation by increasing the interaction between the injectable fluid and the chilled salt water filled particles 340. Other means for agitating the cold slurry can be used, such as vibration and rotation, similar to the cold slurry delivery device 100 of FIG. 3.

In one embodiment, once the salt water filled particles 340 have reached a desirable temperature, the cooling fluid is released from the slurry generation chamber 300 prior to breach of the separation member 360. Once the cooling fluid has been released, the separation member 360 is then breached.

In another embodiment wherein the second compartment 320 is initially empty (e.g., particles 340 are not provided to the second compartment 320), the release of cooling fluid into the second chamber still occurs. In this embodiment, once released, the cooling fluid will flow into the second compartment 320 from the third compartment 330 and will circulate through the second compartment 320. The circulation of the cooling fluid in the second compartment will chill the injectable fluid housed within the first compartment 310, as was disclosed previously.

Figure 13:
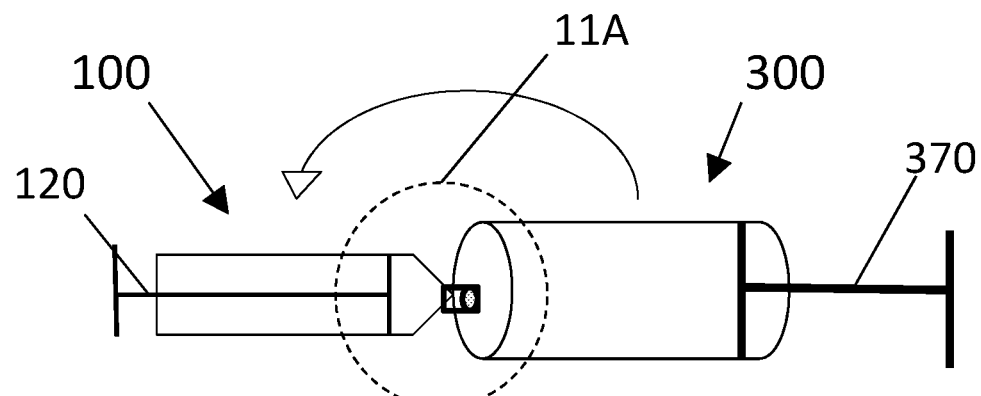
FIG. 13 depicts the transfer of cold slurry from a cold slurry generation chamber to the cold slurry delivery apparatus in accordance with an embodiment of the present invention and FIG. 13A depicts a close up view of the male and female connectors of FIG. 13.
Figure 13A:
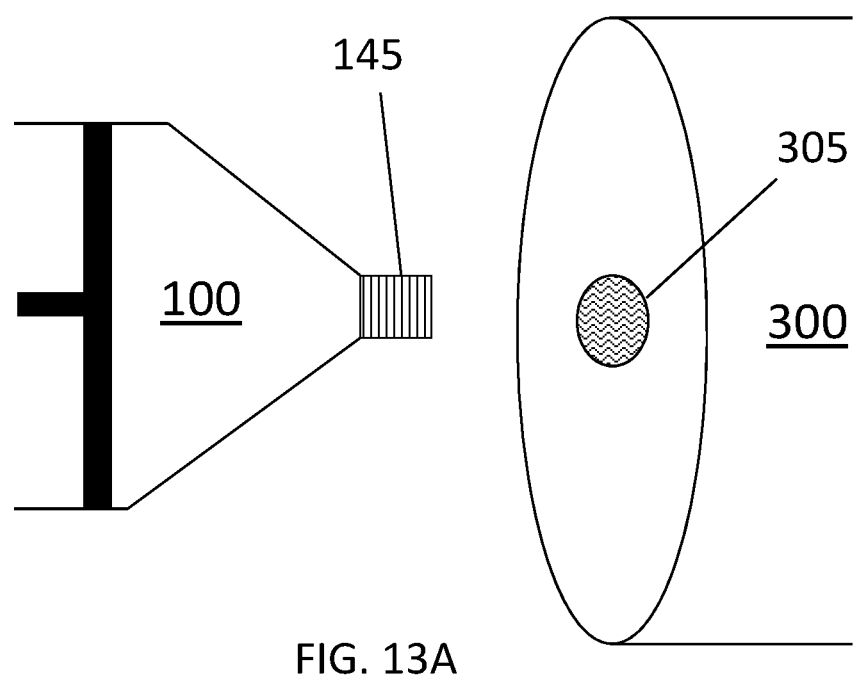

After the cold slurry is formed, the cold slurry can be transferred from the slurry generation chamber 300 to the cold slurry delivery device 100, as shown in FIG. 13. In a preferred embodiment, the cold slurry delivery device 100 and slurry generation chamber 300 mate through male 145 connector and female 305 connector, as shown in FIG. 13A, to removably couple the slurry generation chamber 300 to the cold slurry delivery device 100, with the cold slurry being transferred from the slurry generation chamber 300 through the connectors 145, 305. Transfer can be effectuated through either the pulling of the plunger 120 of the cold slurry delivery device 100 to create negative pressure and/or the pushing of a chamber plunger 370. In the embodiment in which the salt water filed particles 340 are provided to the slurry generation chamber 300, a filter (not shown) can be provided just before the cold slurry exits the slurry generation chamber 300 through the female connector 305. The filter prevents the salt water filed particles 340 from flowing into the cold slurry delivery device 100 with the cold slurry and/or from clogging the opening of the female connector 305. In one embodiment, the slurry generation chamber 300 generates enough cold slurry for a single injection using the cold slurry delivery device 100. In another embodiment, the slurry generation chamber 300 generates enough cold slurry for two or more injections.

Other means for delivering a cold slurry generated in the slurry generation chamber 300 are also contemplated. For examples, a catheter or cannula fitted with connective tubing can be coupled to the slurry generation chamber 300. In one aspect, a battery powered pump can be provided with the slurry generation chamber 300 to effectuate the flow of cold slurry through the tubing and into the cannula/catheter for delivery into a patient's body.

In one aspect of the invention, the fully assembled slurry generation chamber 300 can be provided in a kit along with a device for delivering cold slurry. In this way, the only required actions to generate and deliver cold slurry into a patient's body are to activate the slurry generation chamber 300 and transfer the cold slurry from the slurry generation chamber 300 to the delivery device.

In one aspect of the invention, a temperature sensor is provided to monitor the temperature of the fluid/cold slurry. Any temperature sensor device known in the art, such as thermometers, thermocouples, and other temperature measuring devices can be used in accordance with the present invention. Measurements can be taken internal or external to a container holding the cold slurry. Alternatively or additionally, an additive can be provided to either or both of the cold slurry or the container holding the cold slurry that can change color to indicate that a desired temperature has been reached and/or that the cold slurry is no longer at a desired temperature.

In another aspect of the invention, the cold slurry generated from the apparatuses and methods described above can be provided to a tissue within the body of a patient, for example, for the treatment of a patient. The tissue to which the cold slurry can be administered includes one or more of connective, epithelial, neural, joint, cardiac, adipose, hepatic, renal, vascular, cutaneous, and muscle tissue. Additionally methods include delivery of a cold slurry using and/or generated by the apparatuses described herein to any one or more of the following locations: proximate to a nerve, proximate to subcutaneous adipose tissue, proximate to breast tissue, proximate to visceral fat, fatty tissue proximate to the pharynx, fatty tissue proximate to the palate, fatty tissue proximate to the tongue, proximate to a spinal cord lipoma, proximate to visceral fat, proximate to lipomastia, proximate to a tumor, proximate to cardiac tissue, proximate to pericardial fat, and proximate to epicardial fat. Various conditions, disorders or diseases which can be treated through delivery of cold slurry to a subject include obesity, sleep apnea, nerve pain, and any other disease or disorder such as those disclosed in International Application Publication No. WO/2016/033380, which is incorporated herein in its entirety. Alternatively or additionally, cold slurry can be delivered to a patient in accordance with the invention to improve the aesthetics of the patient through reduction of fat, cellulite, wrinkles, etc., even when the patient is not suffering from a certain condition, disorder or disease.

Figure 14:
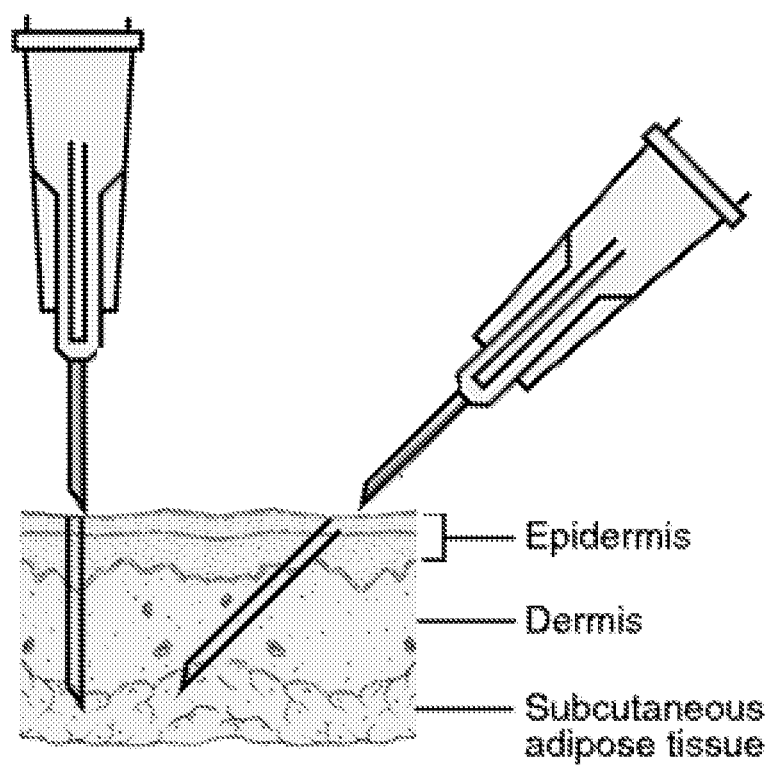
FIG. 14 depicts the delivery of cold slurry to subcutaneous tissue using an apparatus according the present invention.

In a preferred embodiment, the cold slurry is delivered to or adjacent to adipose tissue (fat tissue) within a patient's body in order to induce apoptosis of the tissue cells, as shown generally in FIG. 14. The cold slurry is delivered to the target tissue using a device for delivery of a cold slurry, such as the cold slurry delivery device 100 of FIG. 3 or any other syringe-type device, a catheter or a cannula.

In an exemplary method, an area on a patient's skin through which a device for delivering cold slurry will enter is cleaned and an entry point is marked on the skin. The entry point can be identified, visually, or through the use of one or more imaging technique, such as ultrasound, magnetic resonance, and x-ray. The device is then inserted into the entry point and advanced to the target tissue. The cold slurry is then injected at (or near) the target tissue. An amount of cold slurry can be delivered to multiple sites at (or near) the target tissue. In some instances, injection to multiple sites increases the amount of target tissue that is exposed to the cold slurry and cooled, and can improve the effectiveness of the treatment.

By inducing apoptosis in the tissue cells, fat cells are removed, thus reducing the amount of fat within a patient's body, which in turn can improve the aesthetics of the patient and/or be used to treat obesity (among other diseases or disorders). Adipose tissue comprises white adipose tissue and brown adipose tissue. Adipose tissue can be found just beneath the skin (subcutaneous fat), around internal organs (visceral fat), in bone marrow, intermuscular, and within breast tissue. Areas in which the cold slurry can be delivered to fat tissue include, without limitation, the face, neck, submental area under chin, jowls, eyelids, sub orbital fat pockets, posterior neck (buffalo hump), back, shoulders, arms, triceps, biceps, forearms, hands, chest, breasts, abdomen, flanks (love handles), lower back, buttocks (banana roll), hips (saddle bags), anterior and posterior thighs, inner thighs, mons pubis, vulva, knees, above the knees, calves, shin, pretibial area, ankles, and feet. It is contemplated that the cold slurry can be delivered to any pockets of subcutaneous fat for which reduction of the fat would be desirable.

EQUIVALENTS

While the present invention has been described in conjunction with certain preferred embodiments, one of ordinary skill, after reading the foregoing specification, will be able to effect various changes, substitutions of equivalents, and other alterations to the apparatuses and methods set forth herein.

What is claimed is:

1. An apparatus for delivery of a cold slurry, the apparatus comprising:
    a cylindrical member comprising:
        a first end, a second end, and a longitudinal axis extending through the first and second ends;
        an outer surface extending between the first and second ends along the longitudinal axis; and
        an interior lumen defined by an interior wall of the cylindrical member, the interior lumen configured to receive and hold a cold slurry;
    a plunger at least partially disposed within the interior lumen and configured to move within the cylindrical member in the direction of the longitudinal axis, and the plunger comprising a head, a plunging member, and a rod extending between the head and the plunging member along the longitudinal axis of the cylindrical member;
    at least one needle extending from the second end of the cylindrical member;
    a cooling sleeve surrounding at least a portion of the cylindrical member, the cooling sleeve being configured to cool or maintain a temperature of the cold slurry within the interior lumen of the cylindrical member;
    a removable cap on the cooling sleeve for closure of the cooling sleeve; and
    an agitation device coupled to the plunger and configured to agitate the cold slurry within the interior lumen of the cylindrical member.

2. The apparatus of claim 1, wherein the outer surface of the cylindrical member includes a conductive material.

3. The apparatus of claim 2, wherein the conductive material is copper.

4. The apparatus of claim 1, further comprising a sheath surrounding the cylindrical member, the sheath including a conductive material.

5. The apparatus of claim 4, wherein the conductive material is copper.

6. The apparatus of claim 1, wherein the cooling sleeve and the cylindrical member are in a concentric arrangement with a space formed between an inner surface of the cooling sleeve and the outer surface of the cylindrical member.

7. The apparatus of claim 6, wherein the cap is configured to fit around the first end of the cylindrical member, and to seat with the cooling sleeve towards the first end of the cylindrical member; and
    wherein a seal is provided between the cap and the cooling sleeve.

8. The apparatus of claim 7, wherein a first chemical is provided within an interior space of the cap and a second chemical is provided within the space between the cylindrical member and the cooling sleeve, wherein the seal separates the first chemical from the second chemical, and wherein an endothermic reaction occurs when the first chemical and the second chemical are mixed together.

9. The apparatus of claim 8, wherein the first chemical and second chemical are selected from the group consisting of: water, ammonium chloride, potassium nitrate, sodium thiosulphate, ammonium nitrate, ammonium thiocyanate, and barium hydroxide octahydrate.

10. The apparatus of claim 1, further comprising at least one tubular member located within the space, the tubular member disposed axially about and extending at least partially around a circumference of the outer surface of the cylindrical member, and the at least one tubular member configured to contain a cooling fluid.

11. The apparatus of claim 10, wherein the tubular member is in the shape of a coil.

12. The apparatus of claim 1, further comprising a chamber configured to removably couple and supply the cold slurry to the interior lumen of the cylindrical member.

13. The apparatus of claim 12, wherein the chamber comprises a top end and a bottom end;
    wherein the top end comprising a first connector that mates with a second connector located at the second end of the cylindrical member; and
    wherein the first connector and the second connector are configured to allow the cold slurry to flow from the chamber and into the interior lumen when mated.

14. The apparatus of claim 13, wherein the chamber is configured to produce the cold slurry using a cooling fluid that cools an injectable fluid.

15. The apparatus of claim 14, wherein the chamber comprises:
    a first compartment located at the top end of the chamber and configured to contain the injectable fluid;
    a second compartment located between the top and bottom ends of the chamber; and
    a third compartment located at the bottom end of the chamber and configured to contain the cooling fluid.

16. The apparatus of claim 15, wherein the second compartment is configured to contain salt water filled particles.

17. The apparatus of claim 15, wherein the first compartment and the second compartment are separated from each other by a separation member.

18. The apparatus of claim 17, wherein the separation member is a breakable seal configured to break, such that a content of the second chamber mixes with the injectable fluid in the first compartment.

19. The apparatus of claim 17, wherein the second compartment and the third compartment are in fluidic communication with each other through one or more valves configured to release the cooling fluid in the third compartment into the second compartment when the one or more valves are opened.

20. The apparatus of claim 1, wherein the agitation device comprises a wire extending from the plunging member towards the second end of the cylindrical member along the longitudinal axis.

21. The apparatus of claim 20, wherein the agitation device further comprises one or more tentacles extending out from the wire and toward the interior wall of the cylindrical member.

22. The apparatus of claim 20, wherein the agitation device further comprises a motor coupled to the plunger and configured to vibrate the wire.

23. An apparatus for delivery of a cold slurry, the apparatus comprising:
- a cylindrical member comprising:
  - a first end, a second end, and a longitudinal axis extending through the first and second ends;
  - an outer surface extending between the first and second ends along the longitudinal axis; and
  - an interior lumen defined by an interior wall of the cylindrical member, the interior lumen configured to receive and hold a cold slurry;
- a plunger at least partially disposed within the interior lumen and configured to move within the cylindrical member in the direction of the longitudinal axis, and the plunger comprising a head, a plunging member, and a rod extending between the head and the plunging member along the longitudinal axis of the cylindrical member,
- at least one needle extending from the second end of the cylindrical member,
- a cooling sleeve surrounding at least a portion of the cylindrical member, the cooling sleeve being configured to cool or maintain a temperature of the cold slurry within the interior lumen of the cylindrical member,
- a removable cap on the cooling sleeve for closure of the cooling sleeve; and
- an agitation device comprising least one rotation blade extending from the plunging member towards the second end of the cylindrical member; and
- wherein the agitation device is configured to agitate the cold slurry upon rotation of the plunger.

24. The apparatus of claim 23, further comprising a motor coupled to the plunger.

25. The apparatus of claim 24, wherein the motor is coupled to the rod between the head and the plunging member.

26. The apparatus of claim 24, wherein the motor is coupled to the head of the plunger.

27. An apparatus for delivery of a cold slurry, the apparatus comprising:
- a cylindrical member comprising:
  - a first end, a second end, and a longitudinal axis extending through the first and second ends;
  - an outer surface extending between the first and second ends along the longitudinal axis; and
  - an interior lumen defined by an interior wall of the cylindrical member, the interior lumen configured to receive and hold a cold slurry;
- a plunger at least partially disposed within the interior lumen and configured to move within the cylindrical member in the direction of the longitudinal axis, and the plunger comprising a head, a plunging member, and a rod extending between the head and the plunging member along the longitudinal axis of the cylindrical member,
- at least one needle extending from the second end of the cylindrical member,
- a cooling sleeve surrounding at least a portion of the cylindrical member, the cooling sleeve being configured to cool or maintain a temperature of the cold slurry within the interior lumen of the cylindrical member, and
- a removable cap on the cooling sleeve for closure of the cooling sleeve;
- wherein the cap is configured to engage with and rotate the plunger of the cylindrical member.

28. The apparatus of claim 27, further comprising an agitation device coupled to the plunger and configured to agitate the cold slurry within the interior lumen of the cylindrical member.

29. An apparatus for delivery of a cold slurry, the apparatus comprising:
- a cylindrical member comprising:
  - a first end, a second end, and a longitudinal axis extending through the first and second ends;
  - an outer surface extending between the first and second ends along the longitudinal axis;
  - an interior lumen defined by an interior wall of the cylindrical member, the interior lumen configured to receive and hold a cold slurry;
- a plunger at least partially disposed within the interior lumen and configured to move within the cylindrical member in the direction of the longitudinal axis, and the plunger comprising a head, a plunging member, and a rod extending between the head and the plunging member along the longitudinal axis of the cylindrical member;
- at least one needle extending from the second end of the cylindrical member;
- a cooling sleeve surrounding at least a portion of the cylindrical member, the cooling sleeve being configured to cool or maintain a temperature of the cold slurry within the interior lumen of the cylindrical member, the cooling sleeve and the cylindrical member being arranged concentrically with a space formed between an inner surface of the cooling sleeve and the outer surface of the cylindrical member, the space between the cylindrical member and the cooling sleeve forming a chamber;
- a container surrounding at least a portion of the cooling sleeve and fluidically connected to the chamber, the container configured to hold a cooling fluid and supply the cooling fluid to the chamber;
- at least one inlet located between the chamber and the container configured to allow the cooling fluid to flow from the container and into the chamber;
- a conductive membrane provided between the chamber and the outer surface of the cylindrical member.

30. The apparatus of claim 29, further comprising a release mechanism operably coupled to the at least one inlet to control the flow of the cooling fluid through the inlet.

31. The apparatus of claim 29, wherein the outer surface of the cylindrical member comprises a conductive material; and wherein the conductive membrane and the conductive material are configured to interact with each other when the cylindrical member is received within the cooling sleeve.

* * * * *